US007516714B2

(12) United States Patent
Yamagata et al.

(10) Patent No.: US 7,516,714 B2
(45) Date of Patent: Apr. 14, 2009

(54) IMMOBILIZING DEVICE

(75) Inventors: Yutaka Yamagata, Wako (JP); Toshiro Higuchi, Yokohama (JP); Joon Wan Kim, Shinjiku-ku (JP); Kozo Inoue, Shibuya-ku (JP)

(73) Assignees: Riken, Saitama (JP); Fuence Co., Ltd., Tokyo (JP)

( * ) Notice: Subject to any disclaimer, the term of this patent is extended or adjusted under 35 U.S.C. 154(b) by 208 days.

(21) Appl. No.: 10/493,880

(22) PCT Filed: Nov. 5, 2002

(86) PCT No.: PCT/JP02/11530

§ 371 (c)(1),
(2), (4) Date: Feb. 22, 2005

(87) PCT Pub. No.: WO03/039759

PCT Pub. Date: May 15, 2003

(65) Prior Publication Data

US 2005/0126480 A1 Jun. 16, 2005

(30) Foreign Application Priority Data

Nov. 5, 2001 (JP) ............................ 2001-339593

(51) Int. Cl.
*B05B 5/025* (2006.01)
*B05C 19/04* (2006.01)

(52) U.S. Cl. ...................... 118/50.1; 118/620; 118/625; 118/629; 118/301

(58) Field of Classification Search ................ 118/50.1, 118/620, 625, 629, 301; 427/483; 310/313 R; 347/46; 239/690
See application file for complete search history.

(56) References Cited

U.S. PATENT DOCUMENTS 4,313,343 A * 2/1982 Kobayashi et al. ........ 73/290 V (Continued)

FOREIGN PATENT DOCUMENTS

JP A 5-208150 8/1993

(Continued)

OTHER PUBLICATIONS

Moerman R. et al., "Miniaturized Electrospraying as a Technique for the Production of Mircoarrays of Reproducible Micrometer-Sized Protein Spots," Anal. Chem., 2001, vol. 73, pp. 2183-2189.

(Continued)

*Primary Examiner*—Laura Edwards
(74) *Attorney, Agent, or Firm*—Oliff & Berridge, PLC

(57) ABSTRACT

A solution containing a sample is provided vibration by a vibrating element, the solution is atomized in a status retaining its activities as minute particulate substances, and the solution and/or the atomized minute particulate substances are electrically charged by wires applied a high voltage. Then, the particles are dried out during flying, the particles are deposited onto a substrate grounded by electrostatic force, and to be immobilized in a status keeping its activities.

17 Claims, 24 Drawing Sheets

U.S. PATENT DOCUMENTS

| | | | | | |
|---|---|---|---|---|---|
| 4,527,507 | A | | 7/1985 | Sawai et al. | |
| 4,719,476 | A | * | 1/1988 | Elrod et al. | 347/46 |
| 4,748,461 | A | * | 5/1988 | Elrod | 347/46 |
| 5,191,354 | A | * | 3/1993 | Quate | 347/94 |
| 5,306,412 | A | | 4/1994 | Whitehouse et al. | |
| 5,520,715 | A | * | 5/1996 | Oeftering | 75/335 |

FOREIGN PATENT DOCUMENTS

| | | |
|---|---|---|
| JP | A 7-116575 | 5/1995 |
| JP | A 11-114467 | 4/1999 |
| JP | A 2000-343002 | 12/2000 |
| WO | WO 98/58745 | 12/1998 |

OTHER PUBLICATIONS

Kurosawa M. et al., "Surface Acoustic Wave Atomizer," Sensors and Actuators A, 1995, vol. 50, pp. 69-74.

* cited by examiner

10 μm

A

100 μm

B

A

B

Luminous region

A

B

A

B

IMMOBILIZING DEVICE

BACKGROUND OF THE INVENTION

1. Field of the Invention

The present invention relates to an immobilizing device or method.

2. Related Art Statements

Nowadays, films (thin layers) immobilized biological macromolecules or functional polymers have been widely utilized in an analytical instrument, such as a biochip or a biosensor. In addition, films of functional macromolecules or dyes have been used in various types of leading-edge display devices, optical devices, or semiconductor devices.

Although there has been developed and practically used various devices and techniques for forming such films or thin layers, such conventional devices and methods have not always been applicable to immobilize or deposit biomolecules or of functional macromolecules and to form such films in which activities and functionalities of them are kept due to following reasons.

For example, there are conventional sputtering devices, Electron Beam (EB) resistance heating type vapor deposition sputtering devices, and chemical vapor deposition apparatuses, and they are practically used for forming films of metals or inorganic compounds. However, since in such devices a substance contained in the films must be exposed to plasma or high temperature under high vacuum, if the substance to be processed is biological macromolecules or organic macromolecules it is almost impossible to immobilize or deposit the substance to form a film or a thin layer in which the activities and functionalities of that are kept.

Conventional electrostatic spray apparatus is apparatuses capable of spraying a liquid using pressurized air to deposit the sprayed liquid onto a substrate by electrostatic forces, and it is widely used in coating industry. However, since the conventional electrostatic spray device needs a large amount of liquid due to spraying by pressurized air, almost splayed liquid is wasted. Therefore, such conventional electrostatic spray apparatus is not applicable to form a thin layer of a very small amount of functional macromolecules or biological macromolecules. In addition, since, when a liquid is sprayed using pressurized air the splayed droplets have very large diameters, the splayed droplets will arrive on a substrate without drying. Thus it takes long time to dry the sample contained in the splayed liquid on the substrate, if biological macromolecules, which tend to be denatured or modified in such a long time drying process, are to be sprayed, the splayed biomolecules are most likely to be damaged. Therefore, in the conventional electrostatic spray apparatus, it is hard to immobilize such a substance having a damageable property and to form a thin film in which activities and functionalities of it are retained.

In a conventional spotting device or a coater, solutions are spotted or coated on a substrate using either a pin-like tool made of a metal capable of holding the solutions in a gap like a grove in a fountain pen tip or a coater, and the spotted or coated solutions are dried to form a film. Due to the same reasons i.e., needs of a long time drying process as mentioned about the electrostatic spray apparatus, in the conventional spotting device and coater it is difficult to form a film or a thin layer of substances such as bio macromolecules having properties in which its activities can easily be damaged.

A conventional ink jet method is a method for emitting a jet of a solvent in which target functional polymers are dissolved as minute droplets from a nozzle, to deposit them onto a substrate, and to dry them to form a thin layer. However, due to the same reasons i.e., needs of a long time drying process as the above mentioned techniques, in this method it is impossible to immobilize or deposit to form a thin layer retaining its activities and functionalities of substances such as functional polymers.

The Electro Spray Deposition (ESD) technique is a technique for electrostatically spraying sample solutions to deposit them onto a substrate to form a film, and this ESD technique is disclosed in PCT international publication WO98/58,745. This technique is much more suitable for making a film of substances such as bio macromolecules than other conventional techniques and can form a thin layer retaining its activities or functionalities depending on conditions. However, this technique cannot spray solutions when electrical conductivity of the solution is high and thus there is a problem that films or thin layer which can be formed using this technique are limited to some kinds of samples (refer to a document "Analytical Chemistry, Vol. 73", pp. 2183-2189, 2001). In general bio macromolecules, especially proteins, are dissolved in a buffer solution so as to keep PH constant, electrical conductivity of that is equal to or greater than approximately 1000 μS, and thus in the ESD method it is impossible to immobilize or deposit such sample solutions to form a spots, films or thin layers. In addition, proteins or the like may rapidly lose its activities or functionalities for a short time if a stabilizer such as a buffering agent is removed. When such samples are used for forming s film in the ESD method, if once a buffering agent is removed, a process for making a film must be completed for a short time and thus an operation efficiency will be down. In addition, there is a problem that finished films may have lower activities of samples even if the operations for forming films are done in a hurry. In addition, in the ESD method, in order to pass through a tube of a capillary tip, samples are must almost absolutely be dissolved in a solution. Therefore, in this ESD method, it is impossible to use samples such as particles having a low solubility. Additionally, since the ESD method is a method for spraying solutions as minute droplets utilizing only electrostatic forces of the droplets, a spraying rate is very slow and thus manufacturing speed of the chips or films is slow.

Although it is well known that there has been developed various atomizers or splay devices using different vibrating or oscillating elements for many kinds of purposes, they are just for splaying or atomizing, there has been no attempt to use these vibrating elements as an immobilizing or depositing device.

In order to deposit and immobilize bio macromolecules (such as proteins) or functional polymers to form spots or films while the biologically activities or functionalities of the substances are retained, it is necessary to immobilize and form a film of the substances such that these substances are kept in a condition on which the substance cannot easily be denatured or altered. However, the conventional ESD method or device mentioned above cannot keep such a condition while forming the film. One of the conditions on which the substance cannot easily be denatured or altered is that a liquid containing the substances such as bio macromolecules is extremely quickly dried. However, in general, a liquid at normal temperature is slowly evaporated and the liquid coated on a substrate is not rapidly evaporated even if with vacuum. Although one of the methods for rapidly drying a liquid is that the liquid containing target samples is heated, there is a problem that almost bio macromolecules and functional polymers are altered or denatured by heat treating, and thus biological activities and functionalities of that may be damaged.

Although there is a conventional method, such as a freeze dry, for making a solid from solution containing bio macromolecules and the like, according to this freeze dry method it is impossible to form a film if it is frozen and the frozen substances will normally transform into fine particles. In addition, in case of bio macromolecules or the like which must be dissolved in a buffering solution, or an organic polymers, which have high electrical conductivities, since they have high conductivity, they cannot be processed even by the ESD method and thus it is impossible to form a film of them.

Namely, in any conventional methods or devices it is impossible to form a film of bio macromolecules or functional polymers, in the form of a desired shape or thickness without loosing biological activities or functionalities of that, from small amount of substances.

SUMMARY OF THE INVENTION

It is an object of the present invention to provide a method for forming spots, a film, or a thin layer on a substrate by feeding a solution or an organic/inorganic solvent containing samples such as macromolecules, organic polymers, inorganic substances (e.g., proteins, dyes, or functional polymers), by vibrating them at the same time as charging them to atomize them, by collecting atomized samples to the substrate with electrostatic forces, and by depositing and immobilizing them onto the substrate while biological activities or functionalities of the samples are retained. As used herein, the term "immobilizing" shall be used to describe to form a sold (deposit it), such as spots, a film, or a thin layer on a stable condition, i.e., retaining biological activities or functionalities of the samples and in a dry form, onto a substrate from samples which are dissolved in a solution or dispersed in a solvent.

In order to solve the above mentioned problems, there is provided an immobilizing device, the device comprises:

a vibrating element for vibrating a solution (or a solvent) containing at least one sample (such as functional macromolecules, bio macromolecules, inorganic substances, or organic polymers), to atomize the solution (or solvent) into minute particulate substances whose activities and functionalities are retained;

charging means for electrically charging said solution (or solvent) and/or said minute particulate substances; and supporting means for supporting a substrate on which said charged minute particulate substances are deposited by electrostatic forces.

Alternatively, according to the present invention, there is provided an immobilizing device, the device comprises:

a vibrating element for vibrating a solution (or a solvent) containing at least one sample; and a charging means disposed on said vibrating element for electrically charging said solution or solvent, and the device is configured to atomize the solution (or solvent) into minute particulate substances whose activities and functionalities are kept, by vibrations of said solution (or solvent) with said vibrating element and by electrostatic forces of said charged solution (or solvent) with said charging means, and said device further comprises a supporting means for supporting a substrate on which said charged minute particulate substances are deposited by electrostatic forces.

In other words, the present immobilizing device is characterized in that the charging means is contacted with the solution by placing charging means on the vibrating element and the charging means and the vibrating element are operated simultaneously.

The term "solution (or solvent)" shall be used herein to cover not only for a solution (i.e., water) containing dissolved samples therein but also for other solvents (e.g., an organic solvent such as ethanol or an inorganic solvent, etc.) containing dissolved samples therein. In addition, the term "containing samples" shall be used herein to cover for not only completely dissolved samples but also for dispersed samples in a solution or a solvent.

According to the present invention, it is possible to form or immobilize a film or spots, in which activities of the sample are retained or properties of the sample are not denatured or altered, on a substrate. For example, the present device can be used as a film (thin layer) forming device or micro-array (DNA chip) manufacturing device.

Although the conventional ESD method cannot use a sample solution having high electrical conductivity (in case of solution containing a buffering agent having a high electrical conductivity), since the present immobilizing device according to the present invention atomizes the solution utilizing mechanical vibration and electrical charging at the same time, the present immobilizing device can use a sample solution having high electrical conductivity. Namely, because, when a protein is immobilized or deposited, the present device has no occasion to remove a buffering agent, which acts to retain proteins in a stable state, from the sample solution, the present device has the advantage that there is no need to complete a series of operations regarding forming a film or thin layer in a shot time of period. Additionally the present device can produce a thin layer or a film including a sample(s) having higher activities. In addition, although the conventional ESD method needs a solution containing completely dissolved samples so as to avoid choke up with the non-dissolved samples in an opening of capillary tip, the present device can use a sample having low solubility in a form that the pieces of sample are dispersed in a solution and therefore has a very practical use.

In addition, the present invention can atomize the sample solution at a higher speed and to manufacture chips at a higher rate than those by the conventional ESD technique. For example, although the conventional ESD method can process a BSA solution of 5 μg/μl concentration at a speed of 1 μl/sec, the present immobilizing device according to the present invention using a vibrating element having an atomizing region or site of 5 mm×5 mm can process the same solution at a speed of 10 μl/sec. In the ESD method in order to increase processing capacity, it is necessary to increase the number of capillaries and thus there is a problem that cost becomes too high or more complex maintenance works (for example, it is hard to carry out washing of capillaries) are required with more capillaries. On the other hand, this immobilizing device according to the present invention has the remarkable advantage that it is low cost and it is easy to maintain, because processing speed and atomizing efficiency can easily be increased by just extending an area of the vibrating element in this device. Such a feature of the present device is a synergistic effect by both two technique for atomizing, that is "vibrating" and "charging" (refer to FIGS. 22-25), this is a significant advantage over the conventional techniques.

This synergistic effect is discussed briefly below, but will be explained in detail later. Firstly, a many number of crests on waves are generated in a surface of the sample solution by vibration and minute particles of the solution are formed and jumped out of the crests. At the same time as the vibrating, the forming of the minute particles is urged by repulsion force caused by electrostatics. Additionally the formed minute particles do not make contacts mutually by the electrostatic repulsion force and the minute particles are split into minute pieces or clusters by the electrostatic repulsion force. Due to such a reason, more significant advantage of the synergistic effect of the present device can be obtained than advantage when only one either vibration or voltage is applied, In an embodiment of the immobilizing device according to the present invention, the device further comprises a collecting means for collecting said atomized and charged minute particulate substances by electrostatic forces, and to direct said substances onto said substrate.

According to this arrangement, since the atomized minute particulate substances can efficiently be collected and directed to the substrate, efficiency of the immobilizing is increased.

In another embodiment of the immobilizing device according to the present invention, the device further comprises a means for regulating temperature of at least one of said vibrating element, said substrate, and said solution or solvent.

Alternatively, in a modified embodiment, the device further comprises:

a casing (or a chamber) for fully covering the immobilizing device; and a means for regulating temperature of atmosphere inside the casing and the components (said vibrating element, said substrate, and said solution).

According to the present arrangement, since temperatures of the solution (or solvent), atomized particulate substances, and the deposited sample (such as a thin film) can be controlled, even if a sample in which its activities can be affected by temperature conditions is to be immobilized, such sample can be immobilized with highly keeping its activities.

In yet another embodiment of the immobilizing device according to the present invention, said charging means comprises at least one of a conductive wire, a conductive membrane, a conductive mesh, and a device for emitting charged ions.

According to this arrangement, the solution, the atomized particulate substances, or the particulate substances being atomized can efficiently be electrostatically charged.

In yet another embodiment of the immobilizing device according to the present invention, the device further comprises a liquid supplying means for feeding said solution (or solvent) onto said vibrating element in a predetermined rate of flow.

According to this arrangement, the solution (or solvent) is fed onto the surface of the vibrating element at an appropriate flow rate by a pump or the like, so that the immobilized sample can be manufactured in proportion as a desired atomizing process speed.

In yet another embodiment of the immobilizing device according to the present invention, at least a part of a surface of said vibrating element opposed to said substrate is subjected to a hydrophilic or hydrophobic treatment.

According to this arrangement, the vibrating element is subjected to hydrophilic (or hydrophobic treatment) in response to properties of the solution (or solvent) to be used, or the vibrating element (or its surface) can be made of a hydrophilic material, so that wetting property for the solution can be improved. Therefore, conditions of atomizing the solution can be improved, that is the particulate substances can be split into minute pieces or particle sizes can be equalized.

In yet another embodiment of the immobilizing device according to the present invention, said vibrating element comprises a spreading means for spreading out said solution (or solvent) as a thin layer on said vibrating element.

Conditions or efficiency of the atomizing the solution are improved when the thickness of solution layer on the vibrato surface is decreased. Therefore according to this arrangement, since said solution (or solvent) is spread out as a thin layer on said vibrating element, Conditions or efficiency of the atomizing the solution are improved. In addition, in proportion to the solution layer on the vibrating element is reduced, the solution can be atomized with lower frequency of vibration and thus electricity can be saved.

In yet another embodiment of the immobilizing device according to the present invention, the devices further comprises a particle size control means disposed between the vibrating element and the substrate for controlling sizes of said particulate substances.

Sizes of the particulate substances have much effect on properties of films or spots manufactured. In particular, when the droplets sizes are too large, solvent included in the solution is not completely evaporated till the atomized pieces of the solution are arrived at the substrate and thus activities of the sample are degraded. As just described, although, in many case, samples can stably retain its activities either in a buffer solution or in a dry form, activities of the sample in middle of the drying process will rapidly be decreased. According to this arrangement, in order to rapidly and completely evaporate the sample solution till the sample solution arrives on the substrate, the sizes of the particulate substances can be regulated to desired sizes small enough and to avoid the activities of the sample from degrading. Specifically, the particle size control means can be a mesh having minute holes.

In yet another embodiment of the immobilizing device according to the present invention, said collecting means comprises one or more convergence electrodes disposed between the vibrating element and the substrate.

According to this arrangement, by applying voltage, which has the same pole as the electric charges on the particulate substances, to the convergence electrodes, the convergence electrodes repel the charged particulate substances electrostatically and thus the charged particulate substances are efficiently directed to the substrate and to improve collecting efficiency of the particulate substances.

In yet another embodiment of the immobilizing device according to the present invention, said collecting means comprises one or more masks which are made of an insulating or dielectric material and disposed between the vibrating element and the substrate.

According to this arrangement, desired pattern films can be manufactured depending on shapes of the masks. In addition, when an insulating or dielectric material is used as the mask, once the charged particulate substances are attached on the masks to form a layer having a certain thickness, since then newly pieces of charged particulate substances are not attached due to electrostatic repelling and thus collecting efficiency is improved.

In yet another embodiment of the immobilizing device according to the present invention, the devices further comprises a drying means for drying said particulate substances and wherein said drying means comprises at least one of means for supplying dry air, means for reducing pressure, and means for forming a vacuum.

According to this arrangement, the atomized particulate substances can rapidly be dried and thus the films or spots of the sample, in which its activities are highly retained, can be manufactured.

In yet another embodiment of the immobilizing device according to the present invention, at least a part of a surface, which is faced to the vibrating element, of said substrate is made of a conductive material and is grounded.

Alternatively, in a modified embodiment, said at least a part of the surface made of the conductive material has one or more desired pattern regions.

According to these arrangements, since the grounded conductive material pulls the charged particulate substances, films or the like may efficiently be formed. Additionally, electrical charges of the deposited charged particulate substances are drained away by the grounding.

In addition, when conductive material is placed with a desired pattern (e.g., a spotted pattern) on the substrate surface, in other words, a part of conductive material is exposed on the substrate surface such a pattern, pieces of the particulate substances can be deposited only on the exposed region and thus even if small quantity sample solution is used it may be immobilized. Additionally, since respective formed spots are separated each other, separate regents can easily be dropped to each of spots and thus there is an advantage that functional properties of the sample for various reagents may be tested simultaneously and quickly.

In yet another embodiment of the immobilizing device according to the present invention, said vibrating element is activated intermittently on a predetermined cycle.

According to this arrangement, it is possible to avoid the vibrating element from reaching a high temperature. Since it can be prevented that sample solution, which has a weakness for temperature change, is subjected to high temperature, films or the like having activities, which are more highly retained, may be manufactured.

In yet another embodiment of the immobilizing device according to the present invention, said vibrating element is an ultrasonic transducer, an electrostatic transducer, a piezoelectric transducer, a magneto-striction transducer, an electrostriction transducer, or an electromagnetic transducer.

In yet another embodiment of the immobilizing device according to the present invention, said piezoelectric transducer is a mono-layer structure transducer, a multiplayer structure transducer, or a single crystal transducer.

In yet another embodiment of the immobilizing device according to the present invention, said piezoelectric transducer is a resonant transducer, a surface acoustic wave (SAW) transducer, a length vibration mode transducer, a thickness sheer mode transducer, a radial vibration mode transducer, a thickness vibration mode transducer, or a longitudinal vibration mode transducer.

In yet another embodiment of the immobilizing device according to the present invention, said SAW transducer comprises one or more inter digital transducers (IDTs).

According to this arrangement, since the vibration conditions of the vibrating element can more precisely be controlled due to providing one or more inter digital transducers (IDTs) and as a result the sample solution is minutely atomized, atomization efficiency is increased.

In yet another embodiment of the immobilizing device according to the present invention, the device further comprises a means for feeding said solution or solvent onto a region, at a distance from said IDTs, of said SAW transducer in a predetermined rate of flow, and to hold said fed solution or solvent on a predetermined region of said SAW transducer.

In IDTs of the SAW transducer, if each electrode consisted of IDTs shorts out another one, elastic waves cannot be generated. In order to prevent this, it is necessary to set apart or separate each electrode from other electrodes in a predetermined pitch. Therefore, it is necessary to avoid a sample having high electrical conductivity from contacting an electrode to short out, Consequently, due to that the solution is fed onto a region at a sufficiently distance from the electrodes (i.e., IDTs) as this arrangement, short circuit of the electrodes can be prevented. In order to hold the solution on a certain region, for example, A mesh as a particle size control means or a wire(s) as a charging means is located on or in the vicinity of the vibrating element. Due to arranging the mesh or wire in this way, it can advantageously be prevented that the solution flows out from the vibrating element or flows back to the electrodes. Additionally, a mesh or the like as a particle size controlling means is preferably located on or over the region holding the solution, because the solution is mainly atomized in the region, in which the solution is held therein.

In yet another embodiment of the immobilizing device according to the present invention, said SAW transducer comprises one or more reflectors.

According to this arrangement, due to utilizing effectively surface acoustic waves, the solution can finely be atomized to increase atomizing efficiency.

DETAILED DESCRIPTION OF THE PREFERRED EMBODIMENTS

Several preferred embodiments of the immobilizing device according to the present invention will be described with reference to the accompanying drawings.

The immobilizing device according to the present invention comprises precisely controlled solution supply part for feeding a solution such as a Bio macromolecules solution (e.g., a protein), an organic solution, or polymer solution, an atomizer i.e., atomizing part for providing the solution with vibration energy by means of a piezoelectric transducer or a surface acoustic wave (SAW) element or the like, and to atomize the solution into minute particulate substances (or liquid particles), an electrical charging part for electrically charging the solution and the minute particulate substances being atomizing, and a chip forming part for depositing the atomized particulate substances, and to form chips in various patterns in conformity with masks or the like.

Figure 1:
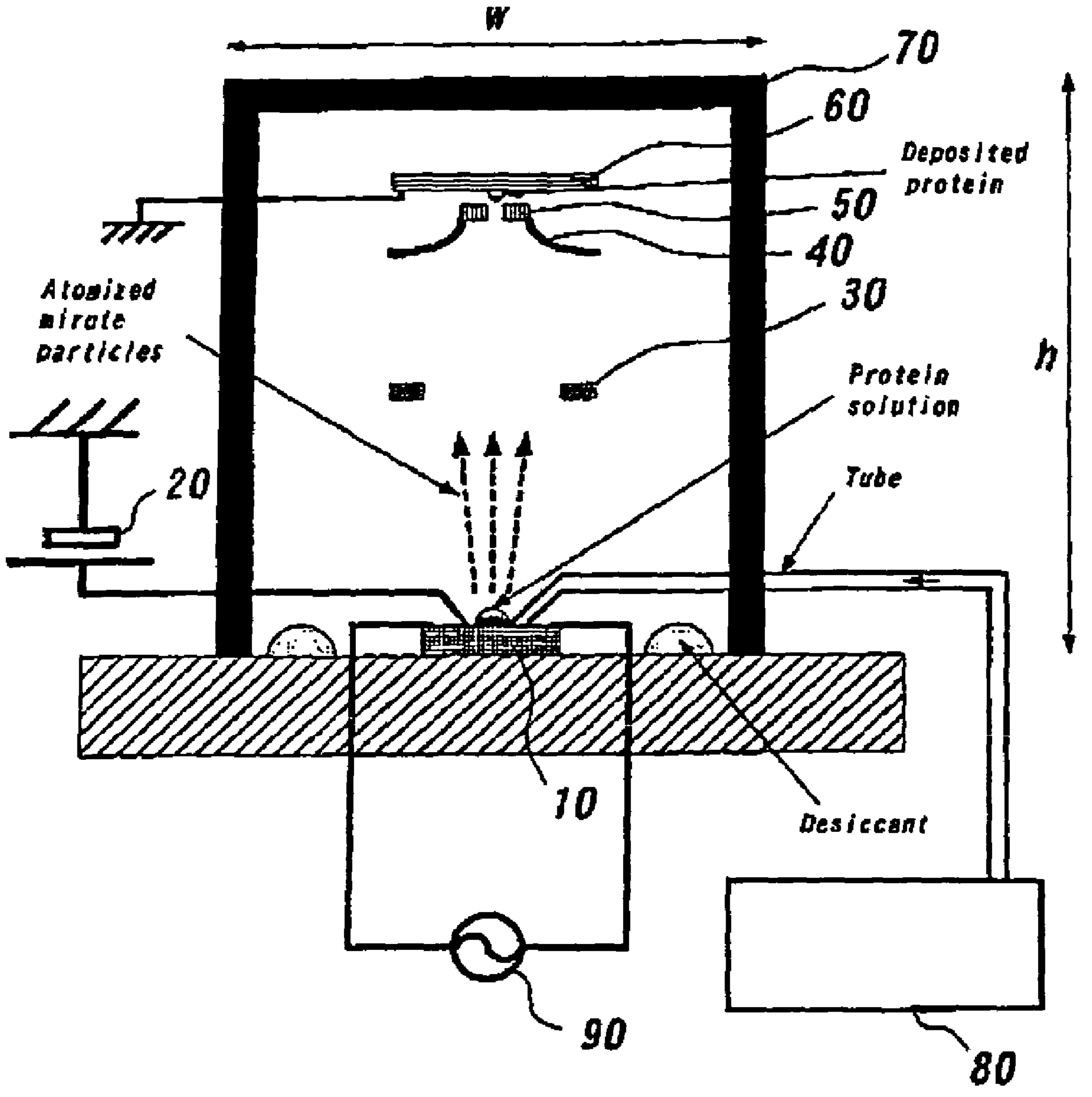
FIG. 1 is a schematic diagram illustrating an exemplary basic configuration of the immobilizing device according to the present invention.

FIG. 1 is a schematic diagram illustrating an exemplary basic configuration of the immobilizing device according to the present invention. As shown in FIG. 1, reference number 10 denotes an atomizer (atomizing part), denotes a high voltage power supply, 30 denotes a collimator electrode(s), 40 denotes a fluorocarbon resin shield, 50 denotes a mask(s), 60 denotes sample chip holder, 70 denotes a chamber (casing), 80 denotes precisely controlled solution supply part, and 90 denotes a high frequency power supply.

As shown in FIG. 1, the atomizer 10 mainly includes a vibrating element (i.e., substrate) having a flat surface. The precisely controlled solution supply part 80 feeds a protein solution onto the flat surface of the substrate in the atomizer 10. A predetermined voltage supplied from the high voltage power supply 20 is applied to the solution on the substrate and as a result the solution acquires electrical charges that is the solution is electrically charged. Alternatively, electrical charging is accomplished after atomized such that the atomized particulate substances are electrically charged. High frequency signal from the high frequency power supply 90 is provided to the substrate in the atomizer 10, due to this signal the substrate (or vibrating element) generates mechanical vibrations therein. Due to the produced vibrations the solution is atomized to be electrically charged particulate substances (i.e., charged fine particles), and to fly out to space in the chamber 70.

The particulate substances are collected and directed to the sample chip holder 60 by the collimator electrode, the fluorocarbon resin shield 40, and the mask 50, to be deposited (or attached) onto the sample chip holder 60 and as a result the deposited or immobilized chip is formed. It is necessary to keep humidity low or dry condition in the chamber 70, in order to dry the atomized particulate substances. Although in this embodiment a desiccant as a drying means is placed in the chamber 70, instead of the desiccant, the drying means can be various devices such as a circulation unit for supplying a dry air and for recovering it, or a decompression (or vacuum) device. Since the atmosphere in the chamber is kept in low humidity and dry condition due to such devices, the atomized particulate substances can more rapidly be dried to improve the activities of the deposit.

Figure 2:
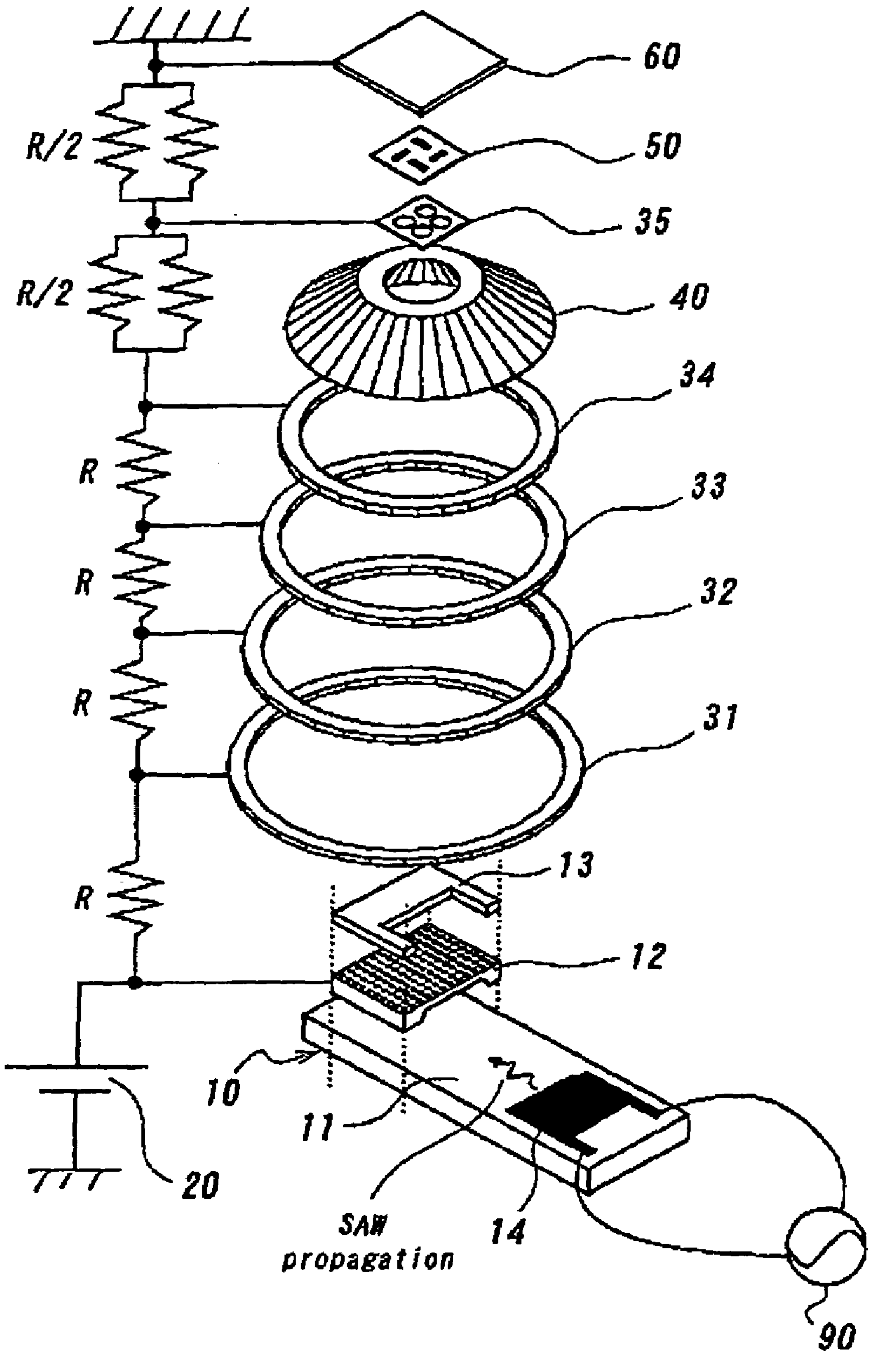
FIG. 2 is an exploded perspective view of an embodiment of the immobilizing device consisting of several components according to the present invention.
Figure 3:
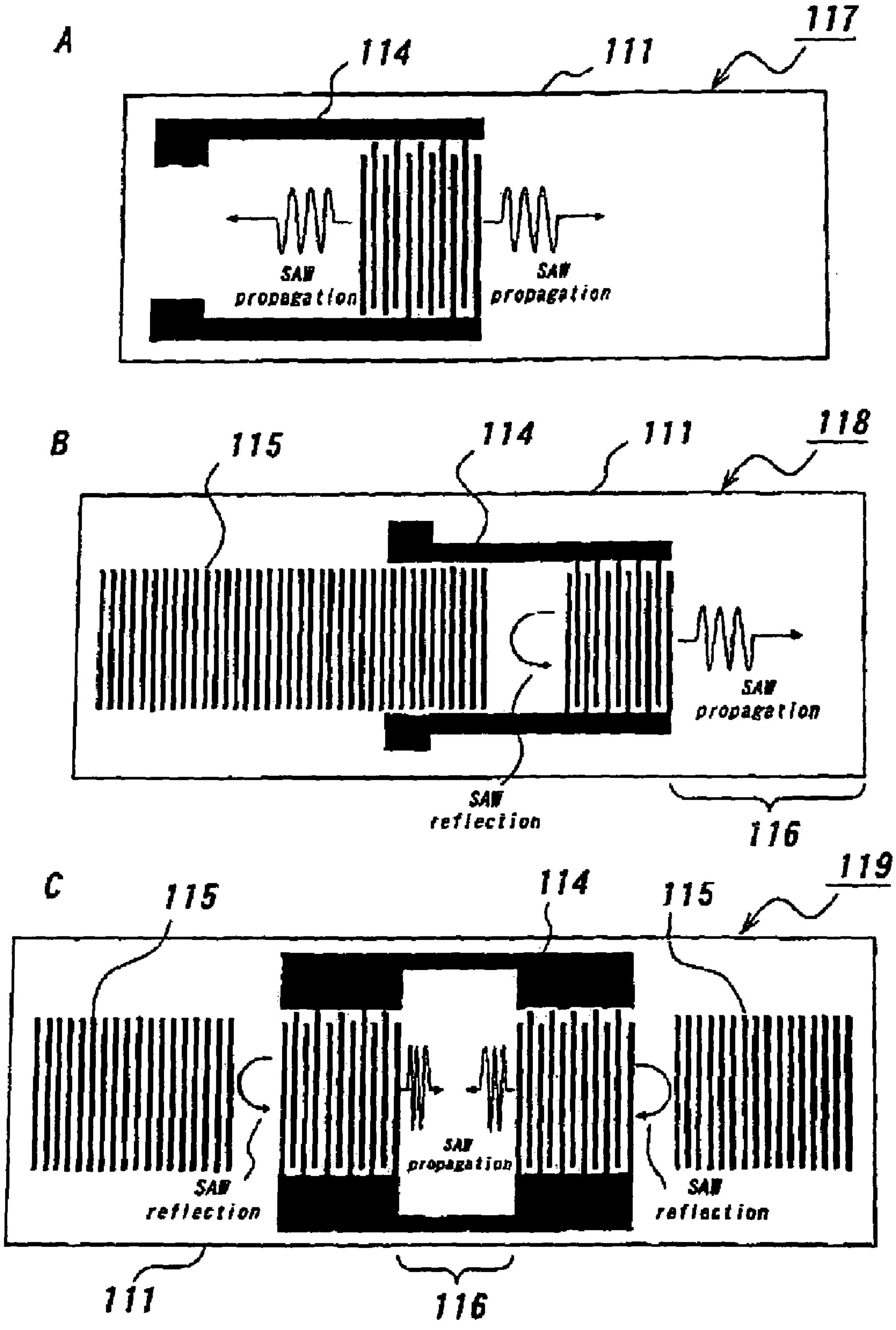
FIGS. 3A, 3B, and 3C are plain views showing respective surface acoustic wave (SAW) elements, which are used as exemplary components consisting of respective atomizers in the devices according to the present invention.

FIG. 2 is an exploded perspective view of an embodiment of the immobilizing device consisting of several components according to the present invention. That is, the FIG. 2 shows a three dimensional assembly diagram of parts from a part for atomizing to a part for forming a chop, comprised in the immobilizing device according to the present invention, and this allows the clarification of ambiguous illustrations in the two dimensional concept view of FIG. 1 by means of the perspective view or three dimensional assembly diagram.

The atomizer 10 shown in FIG. 1 can be various kinds of devices. Although several exemplary atomizers will be shown in detail in FIGS. 3-11, the embodiment of the exploded perspective view in FIG. 2 uses an atomizer of FIG. 6 by way of example. As shown in FIG. 2, the atomizer 10 consists of a piezoelectric substrate 11 (piezoelectric vibrating element), a monolithic structure 12 (i.e., integrated combination of a mesh and spacers) including a mesh having a plurality of holes separately-placed at certain intervals, a holding plate 13, and an IDT 14 (Inter Digital Transducer) which comprises comb-shaped electrodes. When a predetermined high frequency signal is provided to the IDT 14, this electrical signal is converted into elastic waves and this surface acoustic waves are propagated on the piezoelectric substrate 11. A protein solution is fed onto the substrate 11, the fed solution on the substrate 11 is carried into a gap between the mesh 12 and the piezoelectric substrate 11 due to a SAW stream of elastic waves by the IDT 14 and the piezoelectric substrate 11 and as a result the solution layer is kept to a constant thickness, and to be easily atomized. Due to that a surface(s) of the piezoelectric substrate 11, the IDT 14, or the mesh 12 can be subjected to a hydrophilic treatment (or hydrophobic/oleophilic treatment) depending on properties of a solution to be used, wetting properties for solutions can be improved. Thereby it is possible to improve atomizing conditions, that is, to decrease and equalize grain sizes of the particulate substances. Alternatively, instead of these treatments, there can be provided a hydrophilic (or hydrophobic) film laminated on a surface of them.

Although a paper by Minoru Kurosawa, Toshio Higuchi et al. ("Surface Acoustic Wave Atomizer", Sensors and Actuators A 50, 1995, pp. 69-74) describes if a solution layer on a substrate is equal to or more than 1 mm, the solution can not be atomized, it is possible to atomize a solution, in which even if a solution layer is equal to or more than 1 mm, depending on conditions. Although sizes of the atomized particulate substances depend mainly on vibrating conditions, the particle sizes may be determined by other conditions such as sizes of holes in the mesh. Although in this embodiment the mesh having holes with a diameter of 10 m is used, it can be modified as needed and a desired particle size can be obtained by controlling the sizes of the holes in the mesh.

A high voltage power supply 20 in FIG. 2 is electrically coupled to a conductor mesh or spacers and carries out a function of providing the solution and/or the atomized particulate substances with electrical charges. Although in this embodiment the power supply capable of supplying 5000 volts of direct current is used, in practice wide range of voltages can be used. Since voltage impacts on a collecting efficiency, properties, or activities of the formed protein chip, it is preferable that the voltage is optimized.

Although as shown in FIG. 2 there can be provided one or more collimators, in this embodiment there are provided five collimator electrodes 31, 32, 33, 34, and 35. Since collecting efficiency, properties, or activities of the formed protein chip can be affected by conditions such as shapes, the number or spacing of respective collimator electrodes, it is preferable that these conditions are optimized. In this case as shown in FIG. 2, it is preferable that inside diameter of each collimator electrode is gradually reduced as each collimator electrode gets closer to the sample chip holder so that the atomized particulate substances can be collected toward the sample chip holder. In this embodiment they are optimized such that, the collimator electrode 31 has an inside diameter of 80 mm, the electrode 32 has inside diameter of 75 mm, the electrode 33 has inside diameter of 70 mm, and the electrode 34 has inside diameter of 65 mm.

Furthermore, it is preferable that voltage applied to each collimator electrode is gradually reduced as each collimator electrode gets closer to the sample chip holder 60 (i.e., a plate for depositing sample) so that the atomized particulate substances can be collected toward the sample chip holder. For example, in this embodiment when the high voltage power supply 20 feeds 5000 volts of direct current, as shown in FIG. 2, they are optimized such that, the electrode 31 is 4000 volts, the electrode 32 is 3000 volts, the electrode 33 is 2000 volts, the electrode 34 is 1000 volts, and the electrode 34 is 1000 volts by providing appropriate resistances respectively in a circuit.

A fluorocarbon resin shield 40 in FIG. 2 acts as a mask to improve a collecting efficiency. Once electrically or electrostatically charged particulate substances (charged protein) are adhered to the fluorocarbon resin shield 40 to form a layer having a certain thickness of the particles, since then newly pieces of charged particulate substances are not adhered to the fluorocarbon resin shield 40 due to electrostatic repelling between the charged deposited layer and the charged flying proteins and thus collecting efficiency is improved. fluorocarbon resin shield 40 in FIG. 2

In order to drain away (i.e., to ground) electrical charges of the deposited charged particulate substances are drained away, surfaces of the sample chip holder 60 in FIG. 2 preferably have electrical conductivity. For example, the sample chip holder 60 is preferably made of an ITO glass, an aluminium coated PET (polyethylene terephthalate), a stainless material, or single crystal metal. When intending to use a protein chip alone, surfaces of the sample chip holder 60 is preferably coated with a PVP, an EDTA, or the like and thus the deposited chip can easily be broken away from the holder.

FIGS. 3A, 3B, and 3C are plain views showing respective surface acoustic wave (SAW) elements, which are used as exemplary components consisting of respective atomizers in the devices according to the present invention. FIG. 3A shows a SAW substrate 111 and a surface acoustic wave element 117 having an IDT 114, FIG. 3B illustrates a surface acoustic wave element 118 further having an reflector 115 at one end thereof, and FIG. 3C depicts a surface acoustic wave element 119 further having reflectors 115 at both ends thereof.

The piezoelectric material of the surface acoustic wave element is made of 128 degrees rotated y-cut x-propagation $LiNbO_3$. The IDT 114 is provided on the mirror finished surface of the element, the IDT 114 comprises 20 pairs of pieces, which is 100 μm in line width and is 400 μm spacing pitch. Since propagation speed of the Rayleigh wave on the $LiNbO_3$ is 3960 m/s and the pitch of the electrodes is 400 μm, wavelength, which can be determined the electrode pitch, should be 9.6 MHz. Although in this embodiment driving frequency is 9.6 MHz and burst cycle is 1 Hz, and duty ratio is 1 percent, it is possible to atomize in a condition other than those conditions. Since temperature rise of the surface of piezoelectric element is prevented due to driving the piezoelectric element in a burst mode, it can be avoided that the properties of the protein included in the solution, which contacts the element, is degraded. In other words, it is possible to manufacture a protein chip having high activities thereof. Since there is provided the reflector(s) 115 (at one or both ends) as shown in FIGS. 3A and 3B, SAW streams propagating on the substrate are reflected back by the reflector, and to efficiently provide saw streams to an atomizing region 116 and thus atomizing efficiency can be increased.

Alternatively, there are provided several grooves (not shown) at the in the atomizing area 116, the solution is collected to the grooves in the area 116 by utilizing capillary phenomenon and thus the solution can manly be atomized from the area 116.

Figure 4:
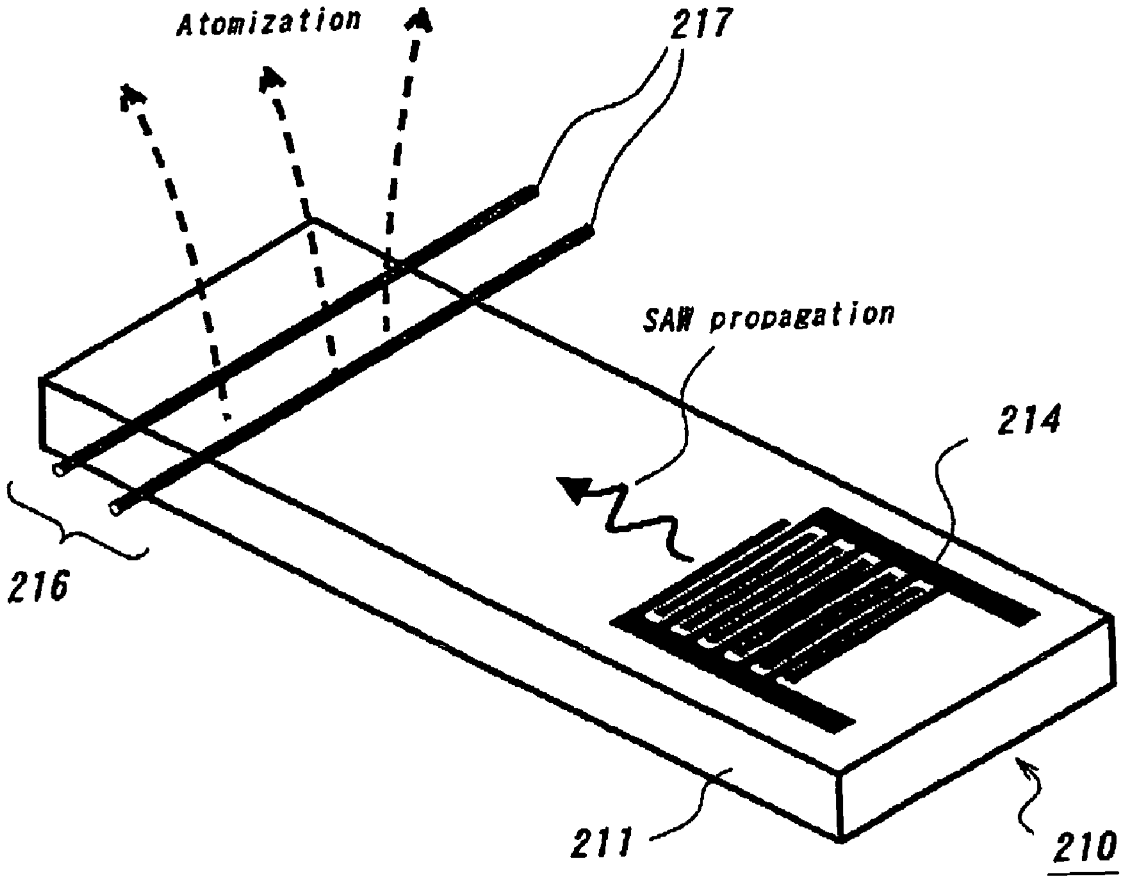
FIG. 4 is a perspective view depicting an atomizer, including wires as a charging means, in the immobilizing device according to the present invention.
Figure 5:
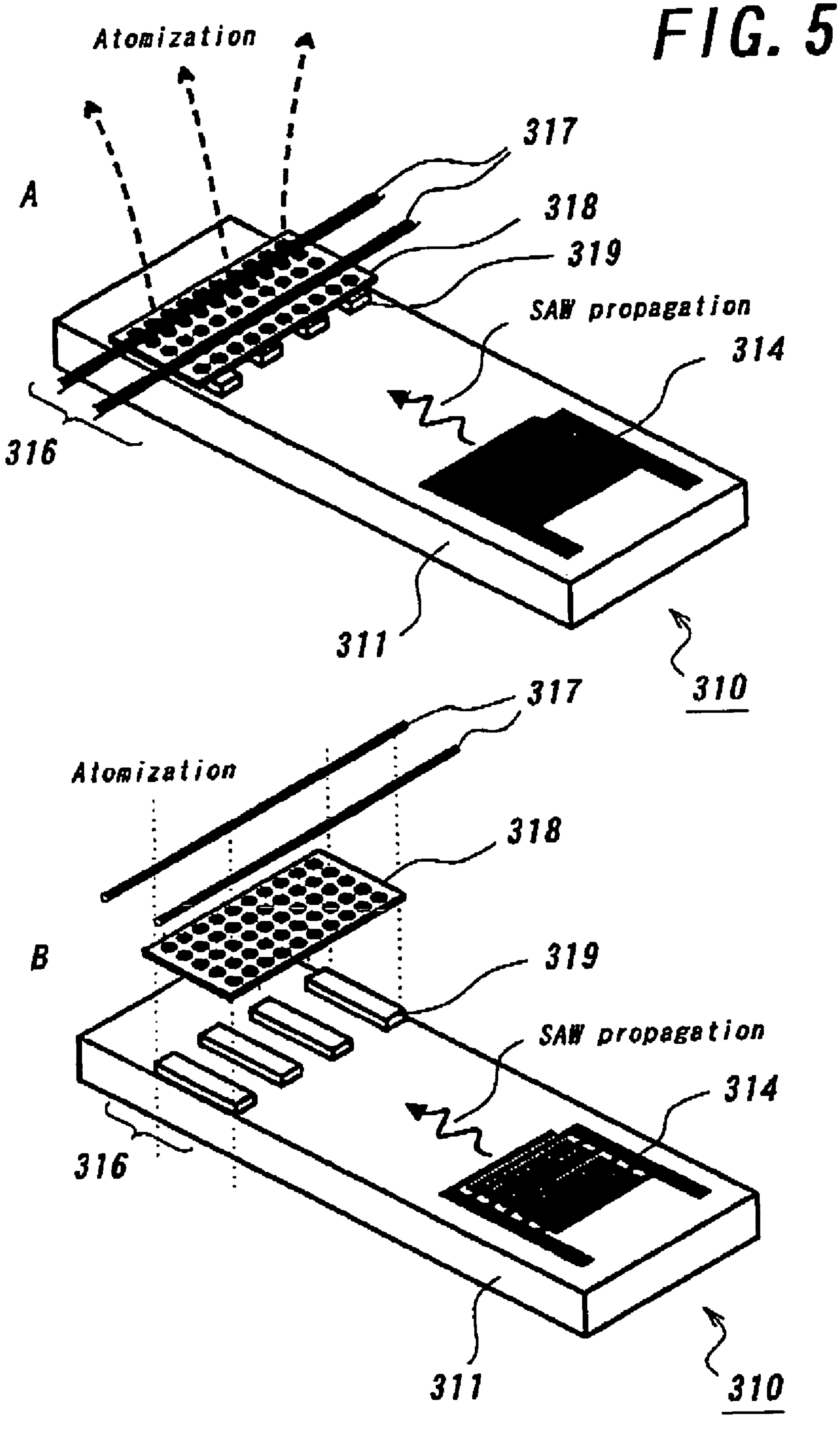
FIG. 5A is a perspective view representing an atomizer, including both wires as a charging means and a mesh as a particle size controlling means, in the immobilizing device according to the present invention.
FIG. 5B is an exploded perspective view showing components in the atomizer of FIG. 5A.

FIG. 4 is a perspective view depicting an atomizer, including wires as a charging means (or as a part consisting a set of atomizing, charging and vibrating), in the immobilizing device according to the present invention. As shown in FIG. 4, an atomizer 210 comprises a SAW substrate 211, an IDT 214 placed on a surface of the IDT 214, and wires 217. Since the solution is mainly atomized and fried out from the left side of the surface of the substrate 211, this area is referred as atomizing region 216 herein. The wires 217, which are connected to a high voltage power supply, is disposed in contact with or above i.e., in the vicinity of the atomizing area 217. However, it is preferable to leave a space between the wires 217 and the surface of the substrate 211, that is, without contacting with the surface thereof, even if the spacing is very short in length. Vibration of the substrate 211 may be attenuated due to the contact. Due to that a predetermined voltage is provided to the wires 217, the protein solution and/or atomized minute particulate substances on the atomizing region 216 are electrically charged to generate charged particulate substances. Alternatively, by providing vibration and charging simultaneously, the solution is atomized into minute particulate substances.

FIG. 5A is a perspective view representing an atomizer, including both wires as a charging means (or as a part consisting a set of atomizing, charging and vibrating) and a mesh as a particle size controlling means, in the immobilizing device according to the present invention and FIG. 5B is an exploded perspective view showing components in the atomizer of FIG. 5A. As shown in FIGS. 5A and 5B an atomizer 310 comprises a piezoelectric SAW substrate, an IDT 314 placed on a surface of the substrate 311, wires 317, a mesh 318, and spacers 319.

The mesh 318 as a particle size controlling means is disposed between a atomizing region 316 of the substrate 311 and wires 317. Thereby, particle size of the atomized particulate substances can be held to a constant. Particle size of the atomized particulate substances is determined by a hole size of the mesh 318. Although in this embodiment the mesh having holes with a diameter of 10 μm is used, it can be modified depending on a desired particle size.

Spacers 319 (in this embodiment aluminium foils are used as the spacers) are disposed between the atomizing region 316 of the substrate 311 and the mesh 318. Thereby, a gap between the mesh 318 and the substrate 311 can be kept to a constant.

Figure 6:
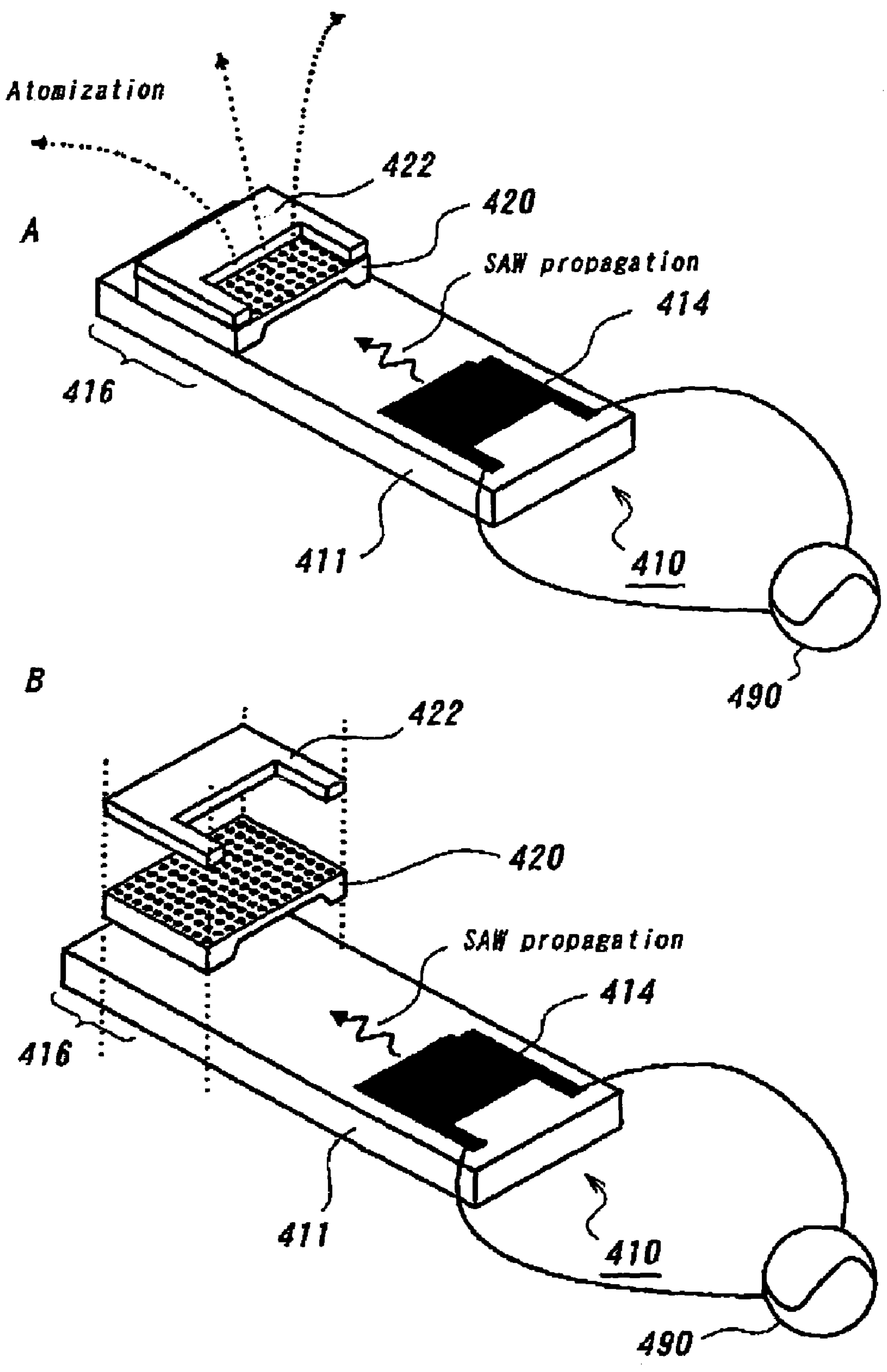
FIG. 6 is a perspective view illustrating an atomizer, including a monolithic structure body integrated a mesh and spacers, in the immobilizing device according to the present invention.

FIG. 6 is a perspective view illustrating an atomizer, including a monolithic structure body integrated a mesh and spacers, in the immobilizing device according to the present invention. As shown in FIG. 6, an atomizer 410 comprises a piezoelectric SAW substrate 411, a IDT 414 provided on a surface of the substrate 411, and a monolithic structure body 420, disposed at the atomizing region 416 on the surface of substrate 411, capable of both a mesh and a spacer. The IDT 414 is connected to a high voltage power supply 490 and a predetermined high frequency signal for driving is provided to the IDT 414.

The monolithic structure body 420 is a component integrated combination of a mesh and spacers, and is manufactured such that, after a block is made by both exposure of SU-8 and plating technology and surface roughness and gap of the block is adjusted by ultra-fine machinery processing. In this embodiment, the monolithic structure body 420 is made of a conductive material and is connected to a high voltage power supply (not shown). Namely the monolithic structure body 420 acts as a charging means, when the solution or the atomized particulate substances make contact with this structure body or pass through the mesh of the structure body, they are electrically charged. Therefore, in this embodiment wires as described above is not needed. Furthermore, there is provided a holding plate 422 on the monolithic structure body 420.

Figure 7:
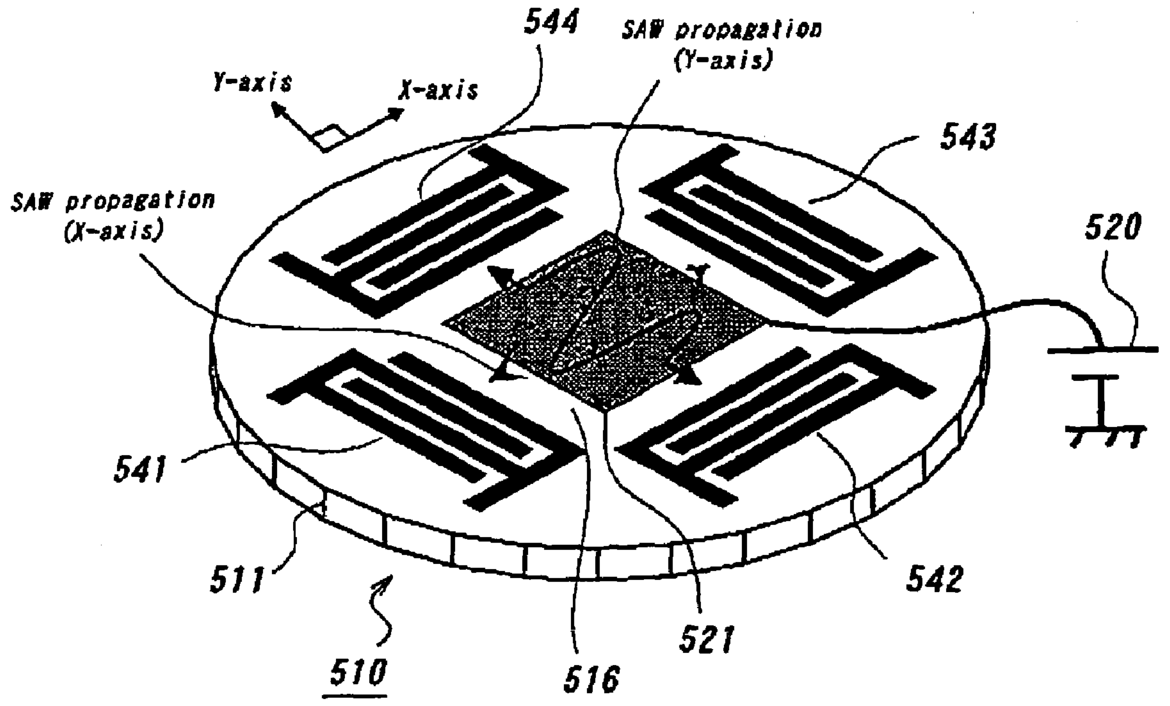
FIG. 7 is a perspective view showing an atomizer, using a two-dimensional surface acoustic wave element, in the immobilizing device according to the present invention.

FIG. 7 is a perspective view showing an atomizer, using a two-dimensional surface acoustic wave element, in the immobilizing device according to the present invention. As shown in FIG. 7, an atomizer 510 (SAW element) comprises a SAW substrate 511, four IDTs 541, 542, 543, and 544 on the substrate 511, as such an atomizing region 516 located at the center of the SAW substrate 511 is surrounded by these IDTs, In an atomizer utilizing surface acoustic waves, the thinner the solution layer is, the lower amount of power is consumed. Therefore, in this embodiment, a pairs of the IDTs 541 and 543, which are facing each other, generates surface acoustic waves (SAWs), which propagates along the direction of x-axis connecting the IDT 541 to the IDT 543, and these SAWs mainly serves to flat (or spread out) the solution layer. According to this arrangement, the solution layer gets thinner and thus the atomizing efficiency can be improved or the particle size of the atomized particulate substances may be decreased.

A remaining pair of the IDTs 542 and 544, which are facing each other, is mainly used for atomizing.

Discrete high frequency signals are separately provided to the respective IDTs, frequency or voltage of the respective signals can separately be set to desired values for any purposes.

There is provided a deposited metal film 521 on an atomizing region 516, the film 521 is coupled to the high voltage power supply 520, and a predetermined voltage is applied to the film, and the solution (or atomized particulate substances in the vicinity of the deposited metal film) is electrically charged.

Figure 8:
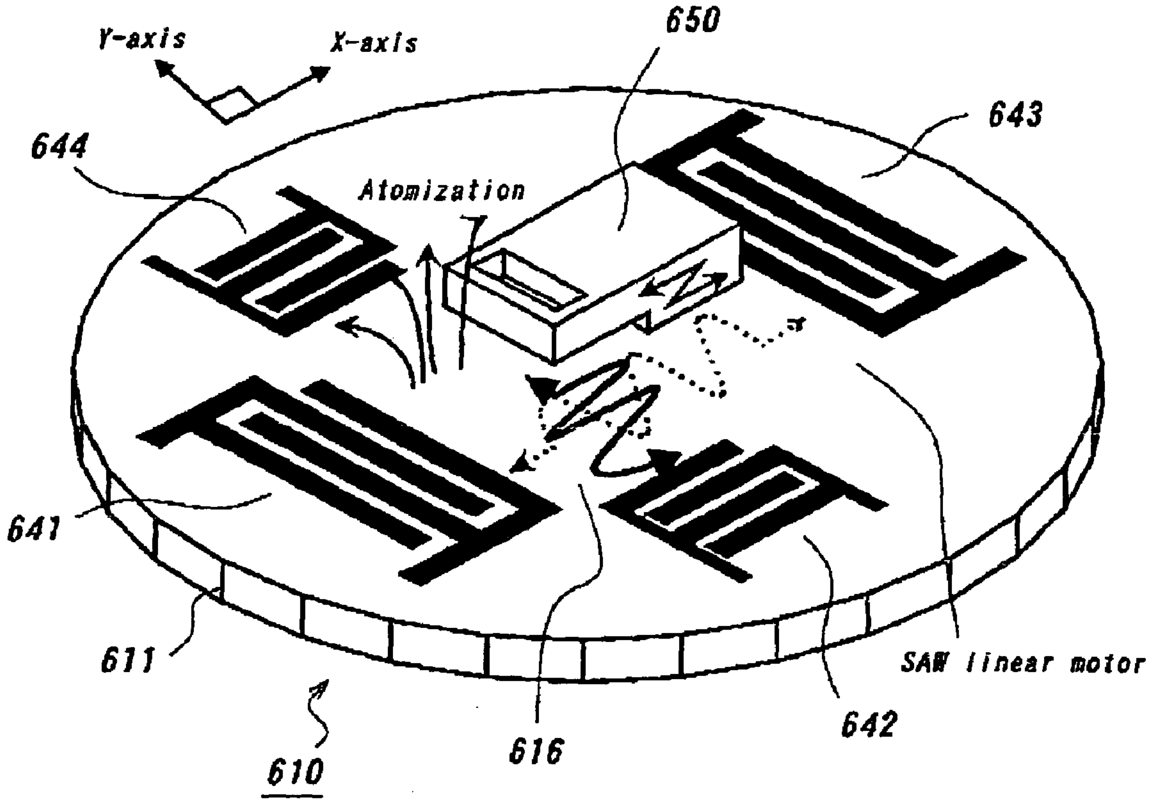
FIG. 8 is a perspective view of a modification of the atomizer of FIG. 7

FIG. 8 is a perspective view of a modification of the atomizer of FIG. 7. As shown in FIG. 8 just like FIG. 7, an atomizer 610 comprises a SAW substrate 611 and four IDTs 641, 642, 643, and 644, on the element 611, as such an atomizing region 616 located at the center of the SAW substrate 611 is surrounded by these IDTs.

Furthermore, a slider 650 is provided on the atomizing region 616 to form a SAW linear motor. Due to that a high frequency signal is supplied to the IDT 641 (or IDT 643), the SAW line motor generates SAWs propagating along with X-axis and thus the slider 650 moves along with X-axis by friction force of the SAWs and the slider 650. When instead of providing the signal to the IDT 641 (or 643), the signal is supplied to the remaining IDT 643 (or 641), SAW direction is inverted and thus the slider moves to the reverse direction. Due to this back-and-forth motion, the solution is flatted and the solution layer gets thinner, and as a result the atomizing efficiency can be improved, or the particle size of the atomized particulate substances may be decreased. In this arrangement, in order to obtain a sufficient friction force, the slider 650 is preferably pressed with proper strength in a direction toward the substrate.

Figure 9:
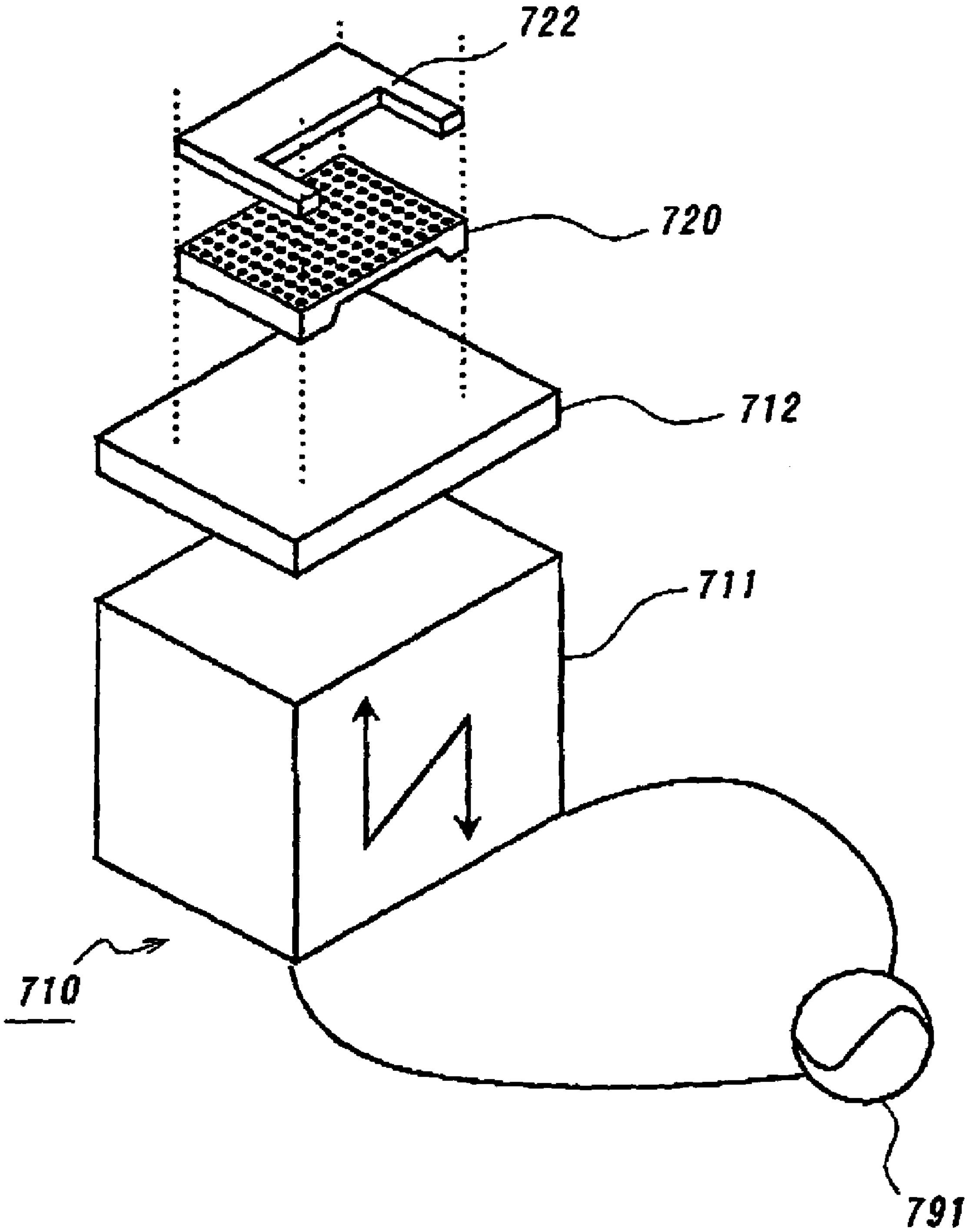
FIG. 9 is an exploded perspective view depicting an atomizer, including a length vibration mode transducer (or oscillator), in the immobilizing device according to the present invention.

FIG. 9 is an exploded perspective view depicting an atomizer, including a length vibration mode transducer (or oscillator), in the immobilizing device according to the present invention. As shown in FIG. 9, an atomizer 710 comprises a piezoelectric substrate 711, a plate 712 disposed on a surface of the substrate 711, and a monolithic structure body 720 serving as both a mesh and s spacer, which is provided on a surface of the plate 712. The piezoelectric substrate 711 is connected to a high voltage power supply 791, when a predetermined electric signal is provided to the substrate 711, mechanical vibration, that is, up-and-down movement is generated by the signal. Due to that the generated up-and-down motion is transferred to the solution on the plate 712 through the plate 712, this arrangement is configured such that the atomized fine particles are fly out from the holes of the mesh.

Figure 10:
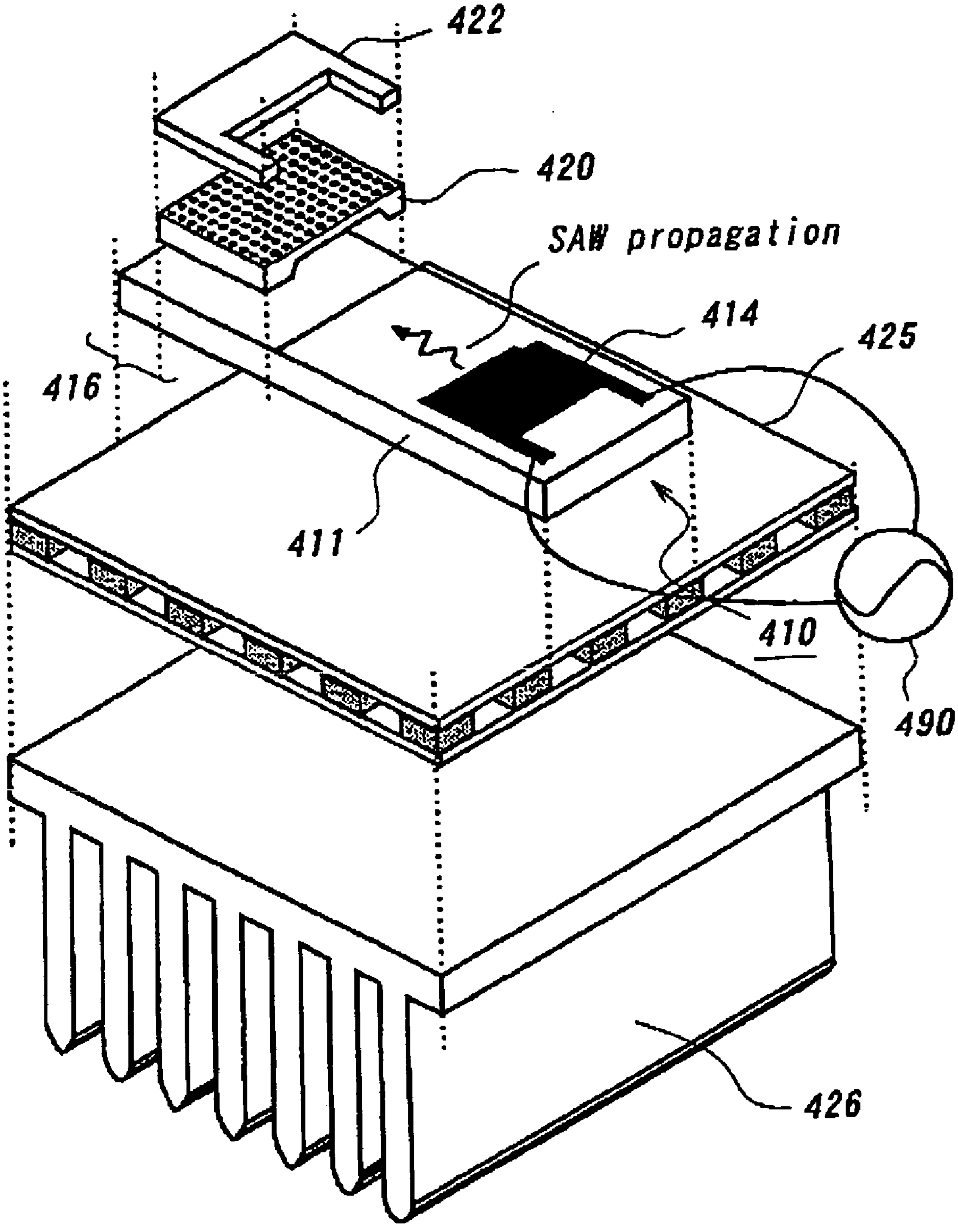
FIG. 10 is an exploded perspective view illustrating an atomizer, including a Peltier element, in the immobilizing device according to the present invention.

FIG. 10 is an exploded perspective view illustrating an atomizer, including a Peltier element, in the immobilizing device according to the present invention. As shown in FIG. 10, the Peltier element 425 is placed at the bottom of the SAW substrate 411 in the atomizer 410 shown in FIG. 6B, and a heat sink 426 is placed at the bottom of this Peltier element 425. For instance, when a solution contains a protein, since activities of the proteins depends on a temperature, the temperature must be controlled. In this circumstance due to mounting the Peltier element 425 on the substrate 411, the temperature of the solution on the substrate can be controlled. Additionally, due to discharging heat to through the heat sink 426, cooling efficiency can be improved. Furthermore, the Peltier element 425 can be mounted to the all atomizers described above, if this element 425 is mounted on, since the Peltier element 425 acts as both a cooler and heater, it is possible to more precisely control the temperature.

Figure 11:
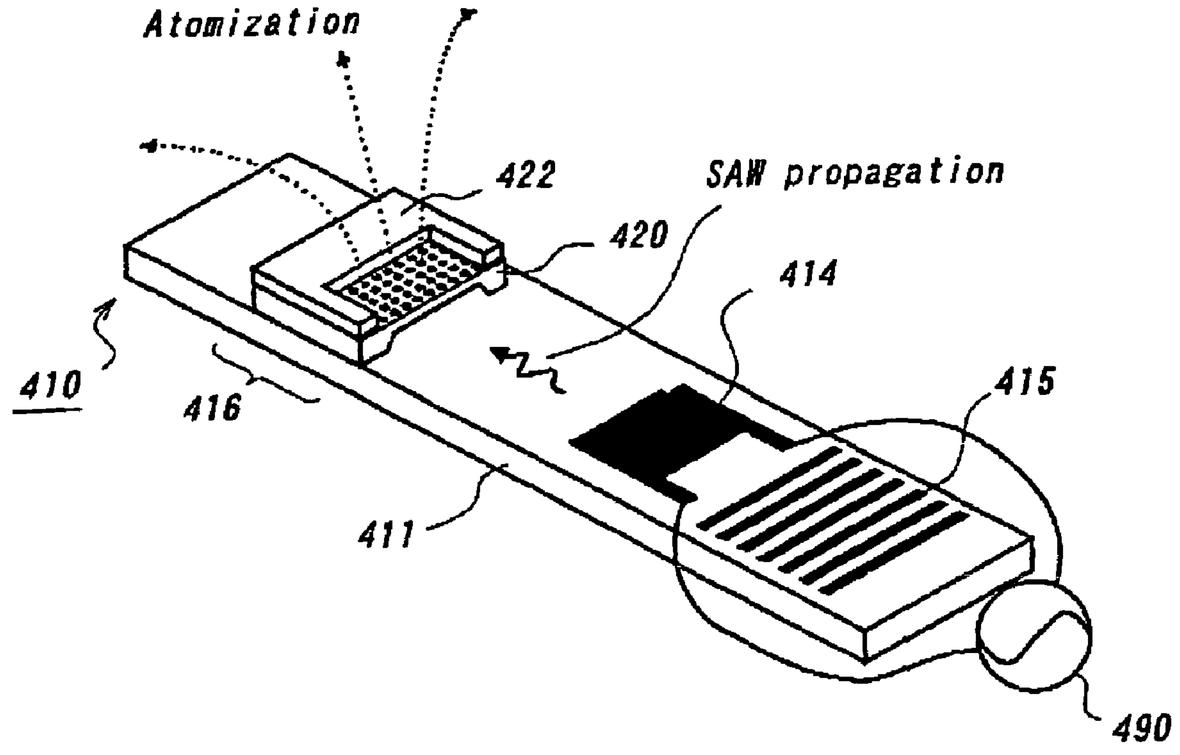
FIG. 11 is an exploded perspective view representing an atomizer, including reflectors, in the immobilizing device according to the present invention.

FIG. 11 is an exploded perspective view representing an atomizer, including reflectors, in the immobilizing device according to the present invention. As shown in FIG. 11, a reflector(s) 415 is placed on the surface of the SAW substrate 411 in the atomizer 410 shown in FIG. 5. When the reflector 415 is provided in this way, surface acoustic waves can efficiently be transmitted to the atomizing region 416, thereby intensity of the vibration may be increased. Therefore, in the last result, it is possible to atomize with a lower voltage and to improve the atomizing efficiency of the solution. Additionally, this reflector can be used for the all atomizers having a SAW element described above.

Figure 12:
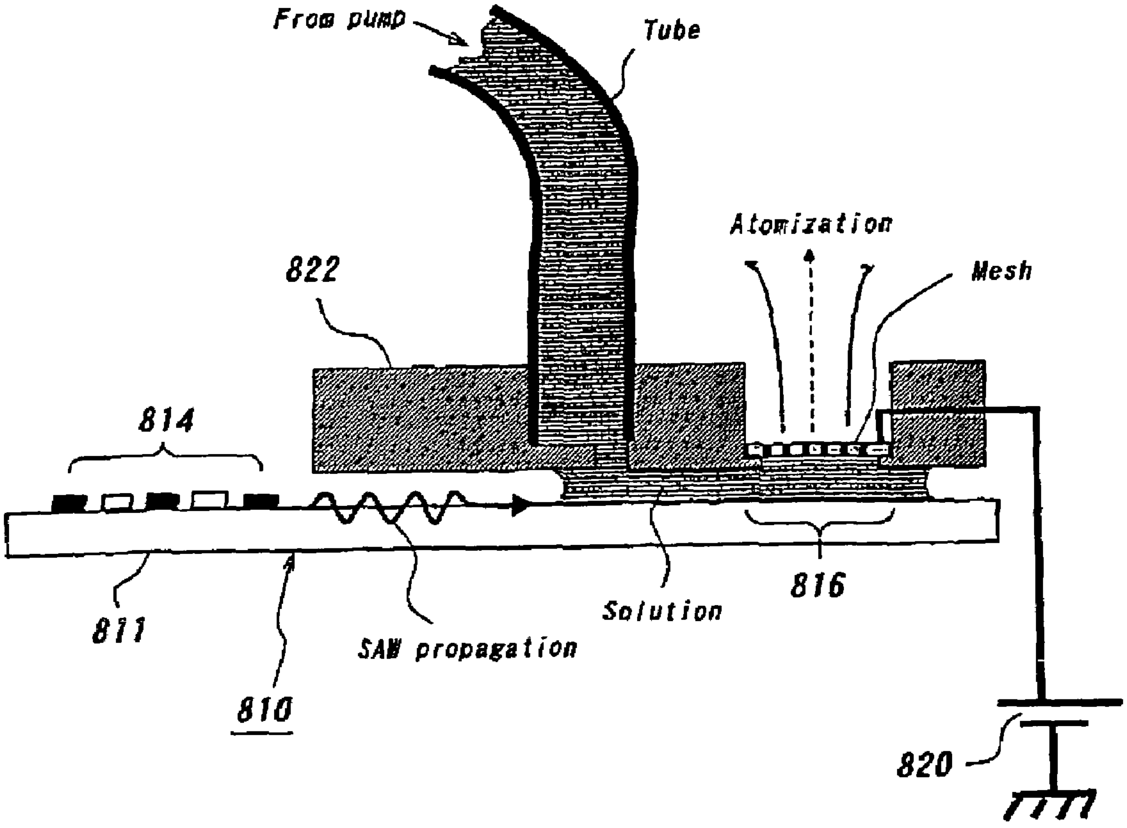
FIG. 12 is a cross-sectional view showing an exemplary atomizer in the immobilizing device according to the present invention.

FIG. 12 is a cross-sectional view showing an exemplary atomizer in the immobilizing device according to the present invention. As shown in FIG. 12, an atomizer 810 comprises a SAW substrate 811, an IDT 814 placed on a surface of the substrate 811, and a container 822 disposed above the substrate 811, which is integrated combination of a mesh and a tube.

A solution containing s predetermined sample(s) is supplied to a gap between the substrate 811 and the container 822 through the tube from a pump (not shown) as a liquid supply means. The supplied solution on the substrate 811 is conveyed to the right side of the substrate, that is, to an atomizing region 816 by a SAW stream propagating from the left to the right on s surface of the substrate. The conveyed solution is atomized in the atomizing region 816 (i.e., beneath the mesh), and the atomized particulate substances are fry out to upward through the mesh. The mesh is connected to a high voltage power supply 820, and the solution or the atomized particulate substances is electrically charged while passing through the mesh.

According to this arrangement, the flow rate of the solution can be controlled to a desired level by adjusting the pump. Furthermore, the flow rate of the solution can be controlled to a desired level by adjusting a intensive of the stream (i.e., controlling a driving voltage).

Figure 13:
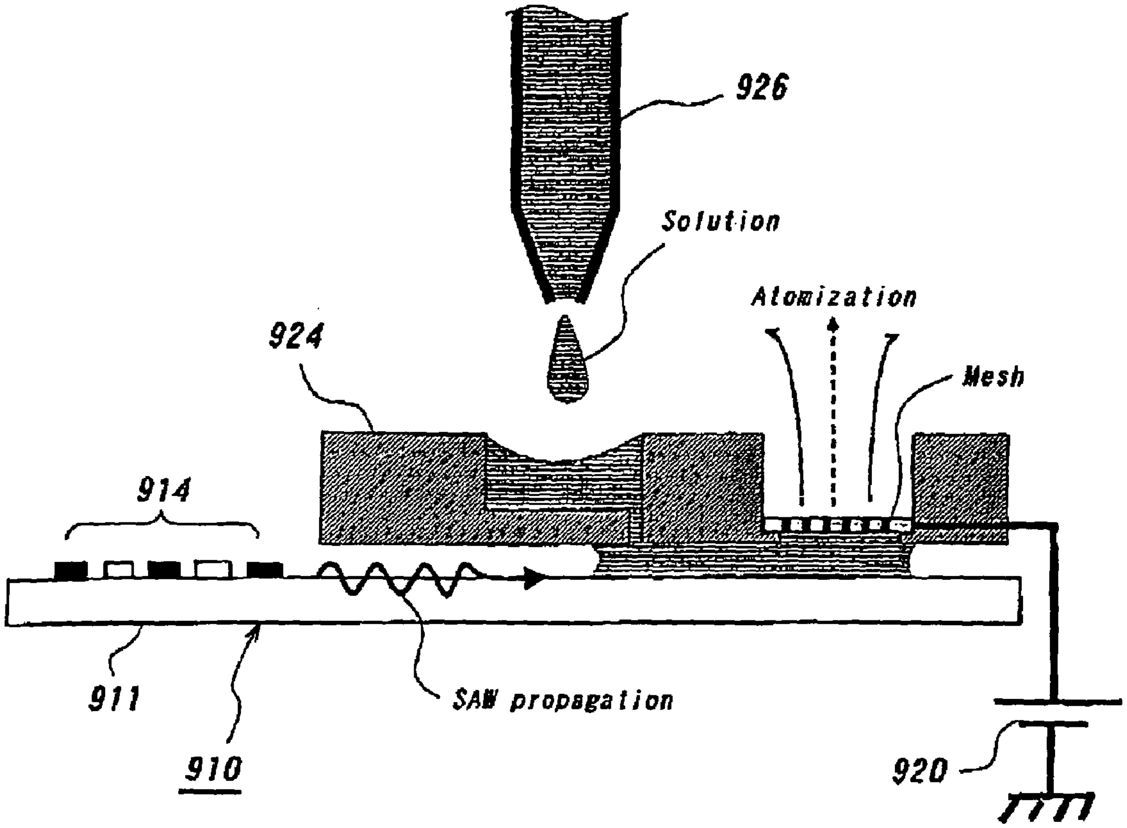
FIG. 13 is a cross-sectional view illustrating a modified atomizer in the immobilizing device according to the present invention.

FIG. 13 is a cross-sectional view illustrating a modified atomizer in the immobilizing device according to the present invention. As shown in FIG. 13, an atomizer 911 comprises a SAW substrate 911, IDT 914 placed on a surface of the substrate 911, and a container 924 disposed above the substrate 911, which is integrated with a mesh. A solution is fed to the container 924 at a proper flow rate in a using an automatic sampler 926. In this way, due to use of the automatic sampler 926, automatic atomizing can be attained while various kinds of solutions can be switched in sequence, or while one of the solution is supplied at a predetermined flow rate. In this embodiment, the mesh is also connected a high voltage power supply 920, and the solution or the atomized particulate substances is electrically charged while passing through the mesh.

Figure 14:
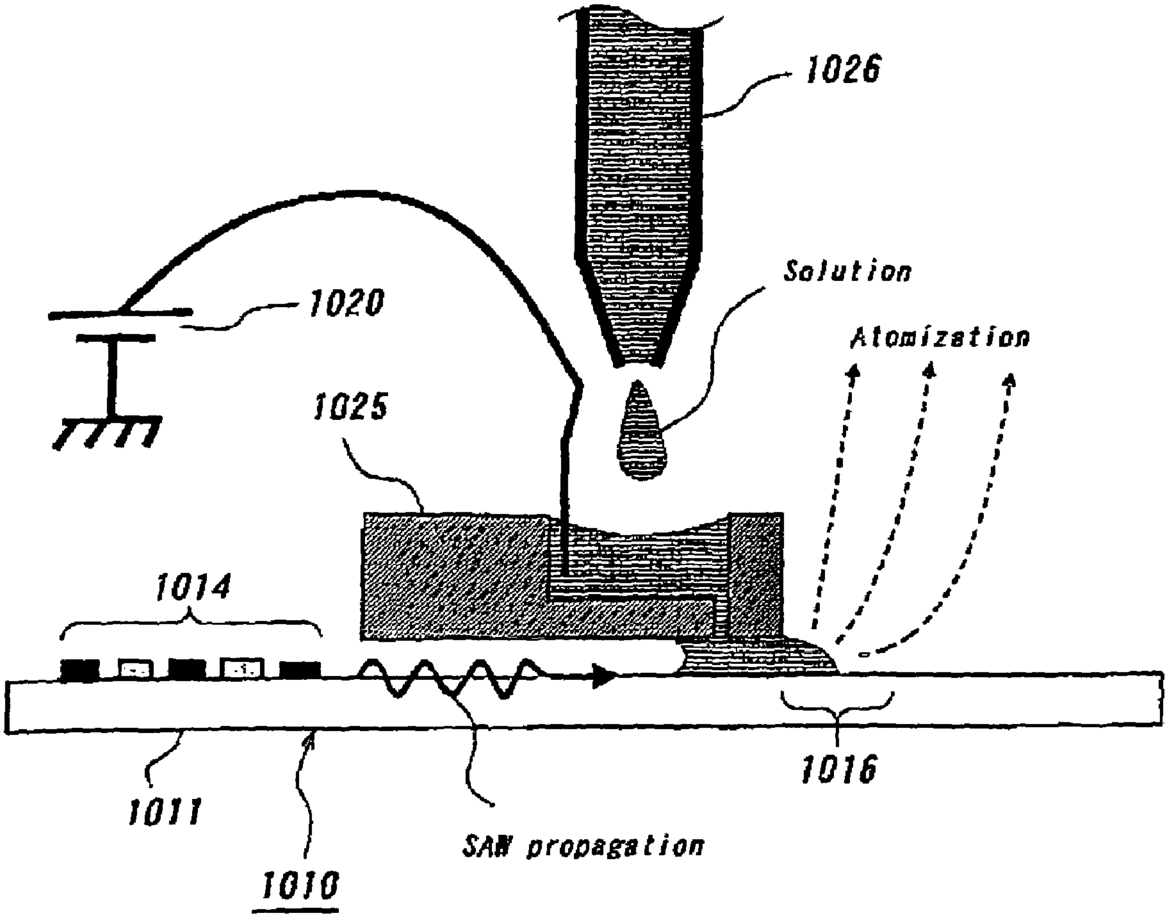
FIG. 14 is a cross-sectional view depicting an exemplary atomizer without a mesh in the immobilizing device according to the present invention.
Figure 15:
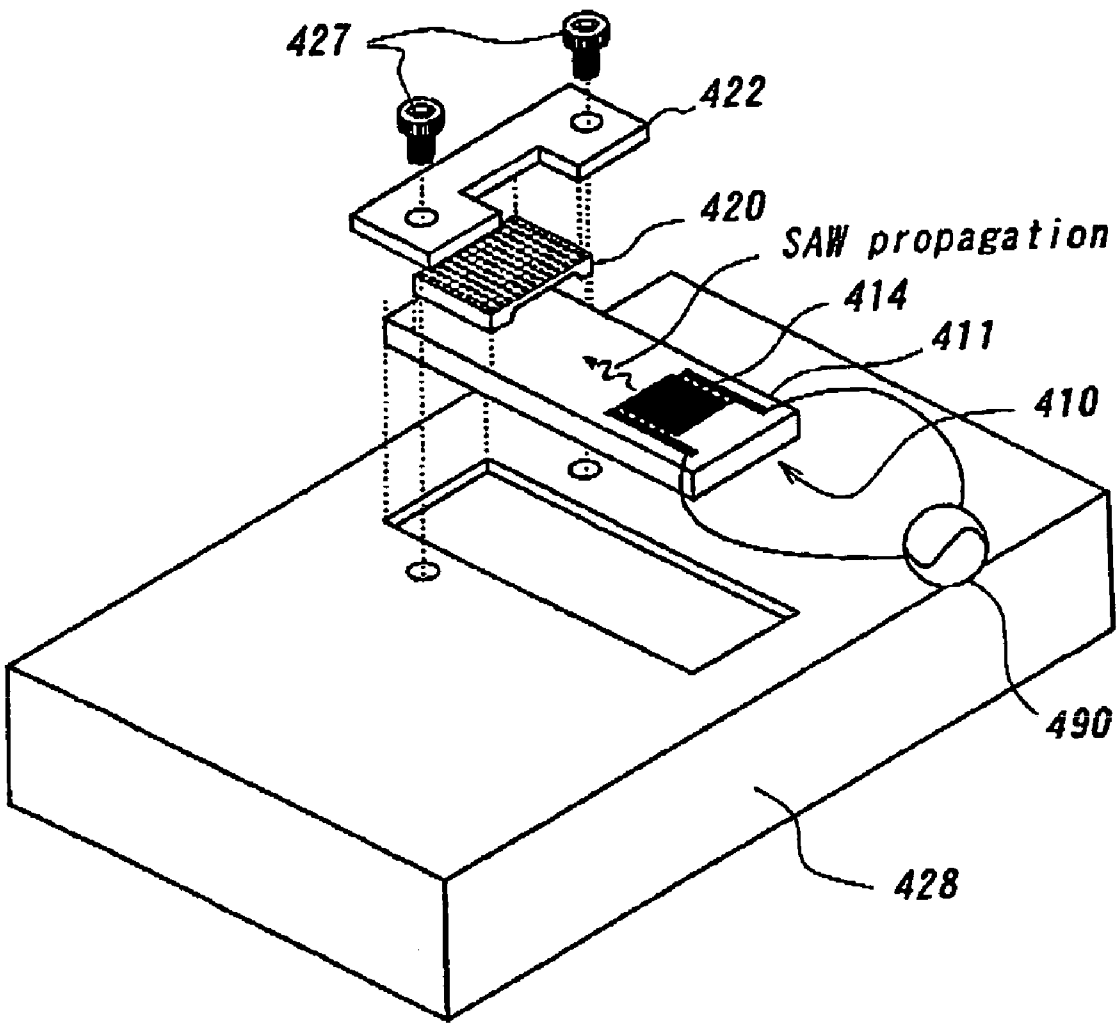
FIG. 15 is an exploded perspective view representing a supporting arrangement, which supports a SAW substrate and a mesh.

FIG. 14 is a cross-sectional view depicting an exemplary atomizer without a mesh in the immobilizing device according to the present invention. As shown in FIG. 14, an atomizer 1010 comprises a SAW substrate 1011, an IDT 1014 placed on a surface of the substrate 1011, and a container 1025 disposed above the substrate 1011. As shown in FIG. 14, a solution is fed to the container 1025 from an automatic sampler 1025. A predetermined voltage from a high voltage power supply 1020 is applied to the solution via a conductive wire and the solution is electrically charged. In this embodiment, since a distance between the container 1025 and the substrate 1011 is sufficiently small, vibration caused by SAW propagation may easily atomize the solution in an atomizing region 1016 or in the vicinity thereof FIG. 15 is an exploded perspective view representing a supporting arrangement, which supports a SAW substrate and a mesh. As shown in FIG. 15, the atomizer 410 shown in FIG. 6A is mounted on a base plate 428. Due to that a holding plate 422 at the top of the atomizer 410 is fixed to the base plate 428 by screws 427, the atomizer 410 is fixed to the base plate 428. In this case if an adhesive bond is used on a surface of the SAW substrate for fixing, it is undesirable to use an adhesive bond since an energy of SAWs should be absorbed. Therefore, it is preferable that the atomizer is mechanically fixed and supported like this embodiment. However, various supporting techniques other than that used in this embodiment can be applicable to this device.

Figure 16:
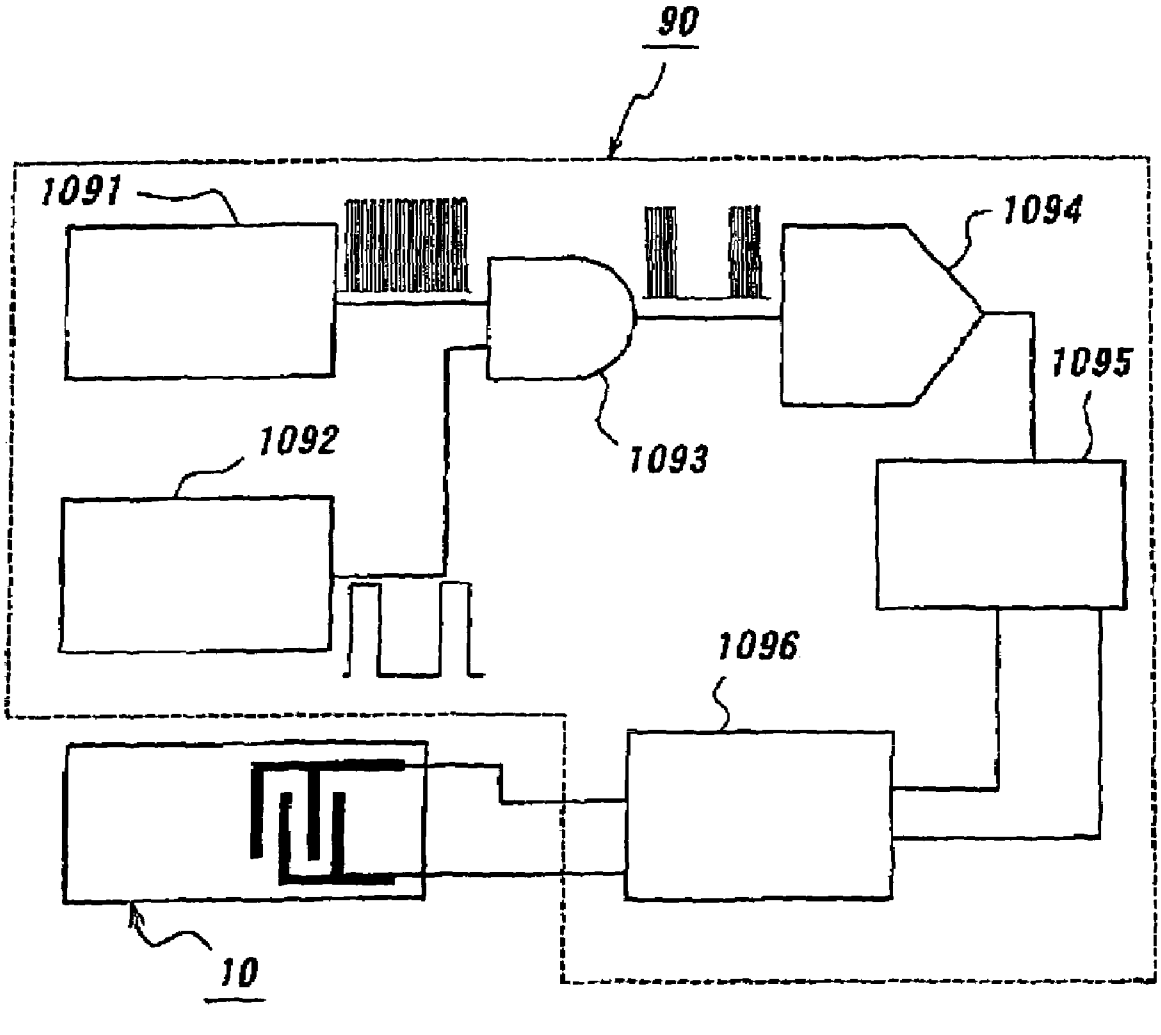
FIG. 16 is a block diagram illustrating a exemplary high frequency (RF) power source used by the immobilizing device according to the present invention.

FIG. 16 is a block diagram illustrating a exemplary high frequency (RF) power source used by the immobilizing device according to the present invention. As shown in FIG. 16, a high frequency power source 90 comprises an oscillator for main frequency 1091, an oscillator for intermittent driving 1092, an AND circuit 1093, a preamplifier 1094, a main amplifier 1095, and an impedance matching circuit 1096.

An AND operation is performed on a signal from the oscillator for main frequency 1091 and a signal from the oscillator for intermittent driving 1092 in a predetermined duty ratio, to generate a high frequency signal, and the high frequency signal is supplied to an atomizer 10 through the preamplifier 1094, the main amplifier 1095, and the impedance matching circuit 1096. The supplied high frequency signal drives the SAW substrate to generate vibrations.

Figure 17:
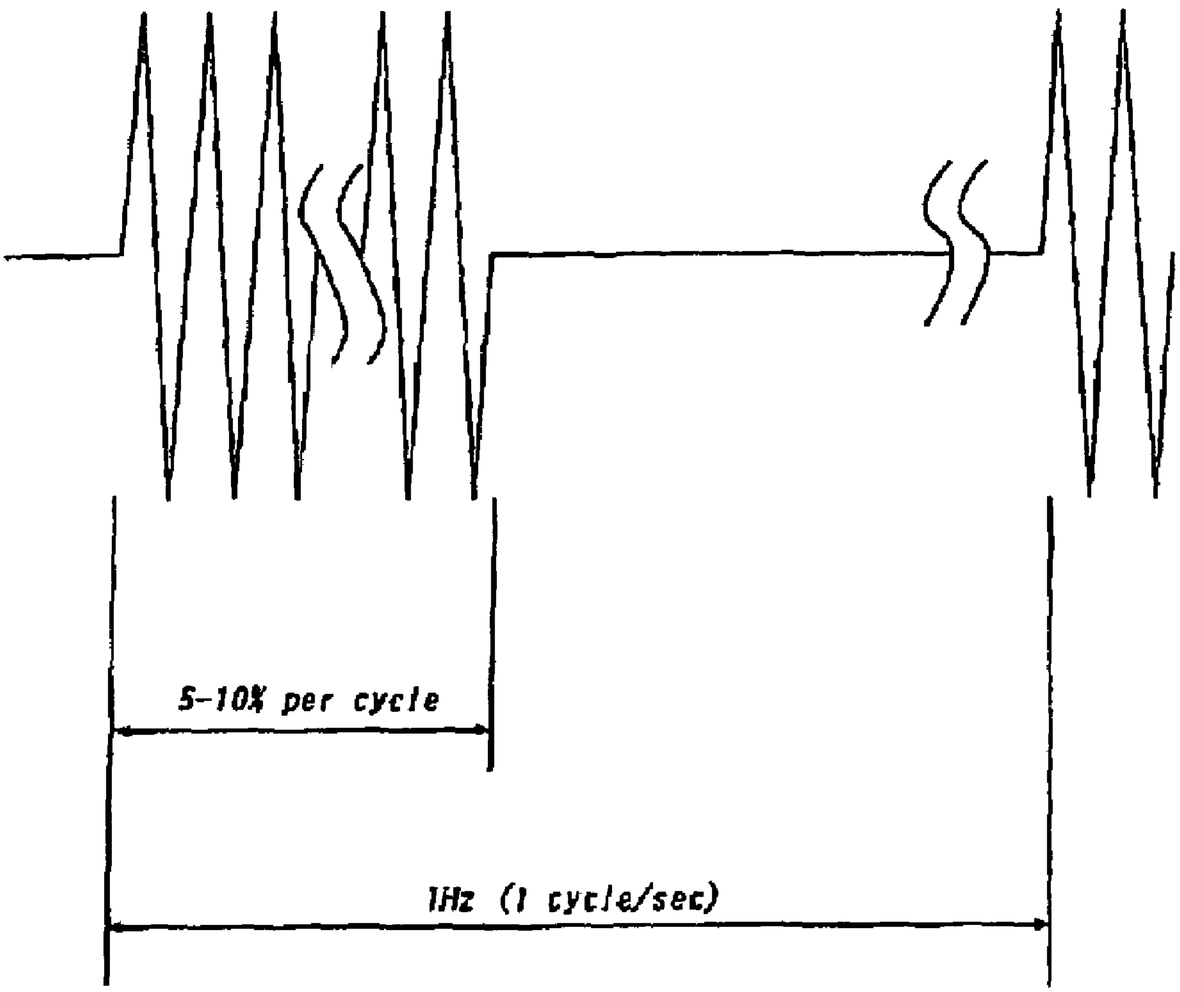
FIG. 17 is a wave form chart of an exemplary waveform of driving voltage in burst mode, which is supplied to a vibrating element in the immobilizing device according to the present invention.

FIG. 17 is a wave form chart of an exemplary waveform of driving voltage in burst mode, which is supplied to a vibrating element in the immobilizing device according to the present invention. As shown in FIG. 17, the oscillator for intermittent driving 1092 generates a driving voltage signal for burst mode in a desired duty ratio. The duty ratio is preferably set to approximately 5-10 percent. Therefore, when the SAW substrate is driven intermittently, due to that an appropriate vibration is generated while temperature rise of the SAW substrate is prevented, the solution can be atomized.

Figure 18:
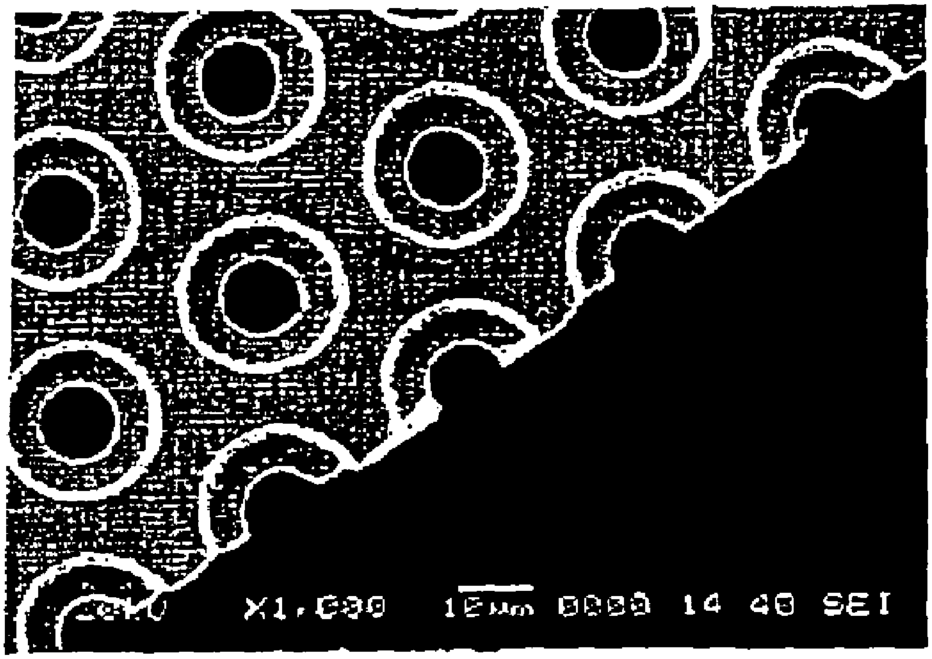
FIGS. 18A and 18B are two separate magnifications of a micrograph obtained by scanning electron microscope (SEM) of a mesh, which is used in the immobilizing device according to the present invention.
Figure 18:
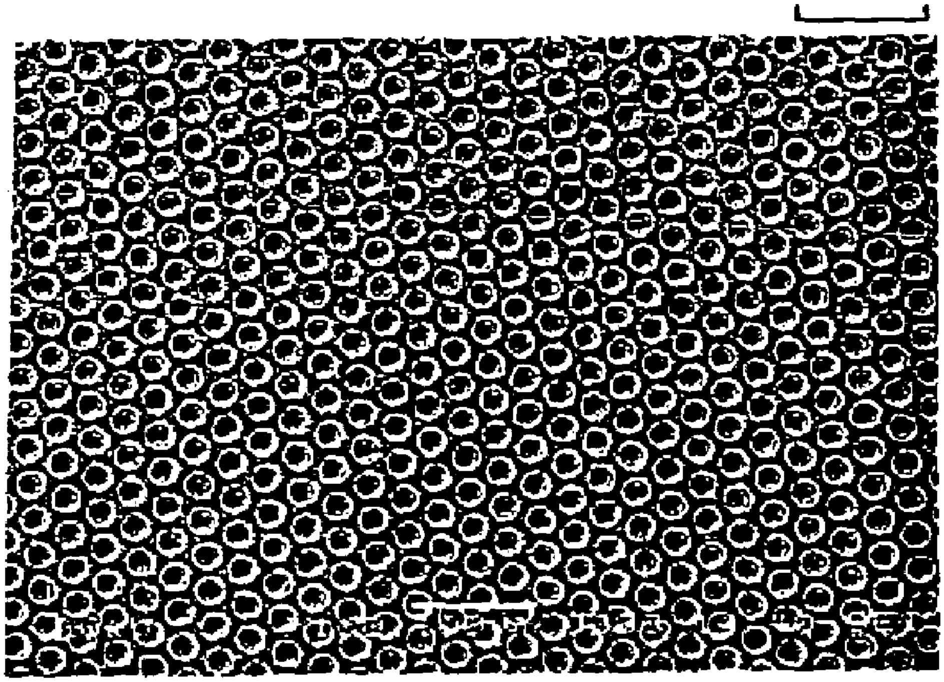

FIG. 18 is a micrograph obtained by scanning electron microscope (SEM) of a mesh, which is used in the immobilizing device according to the present invention. A mesh is processed by a micro machining and inside diameter of the boles in the mesh is 10 μm. This mesh acts as a particle size regulation means. Although in this embodiment the mesh of 10 μm is used, various kinds of meshes can be used depending on a desired particle size.

Figure 19:
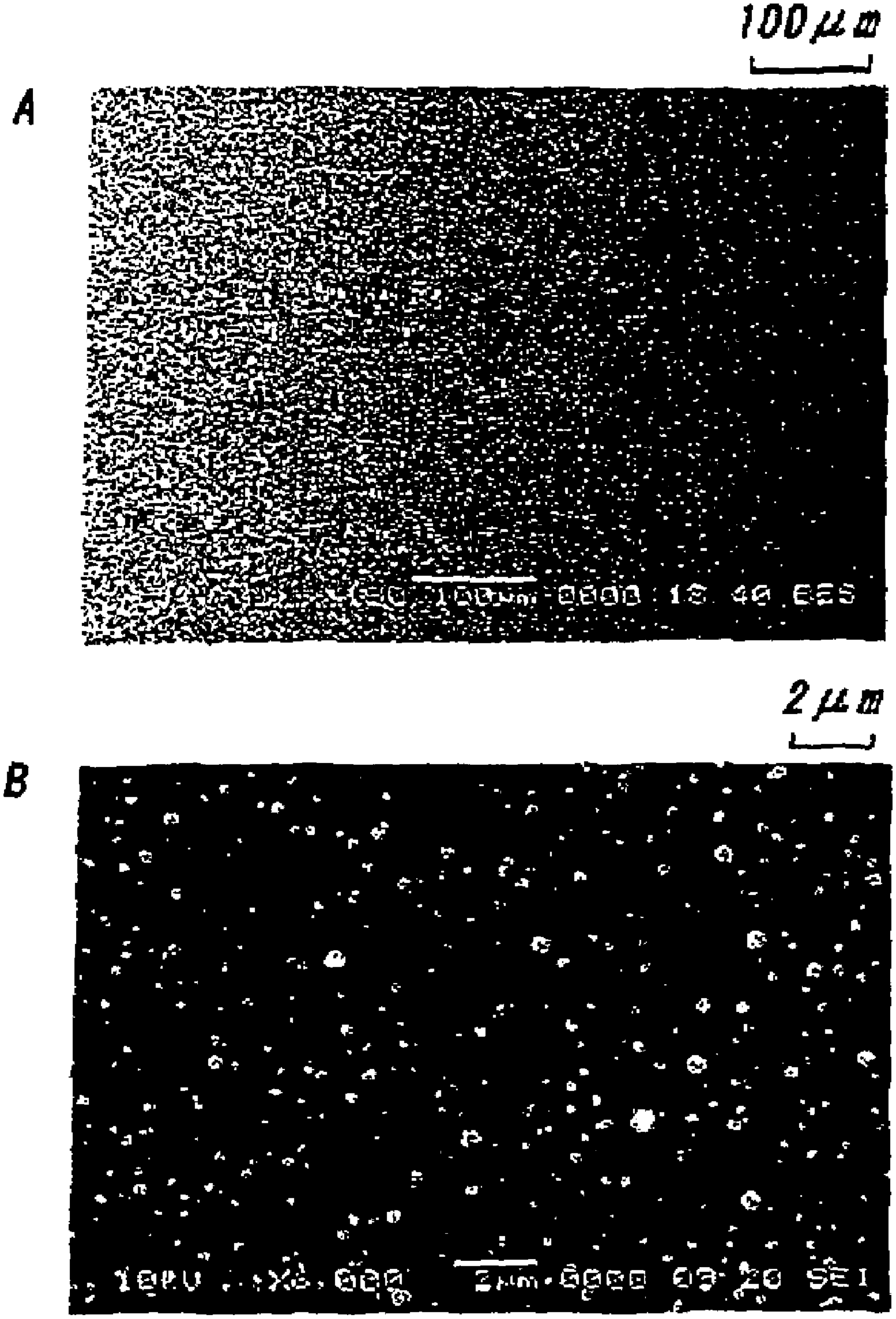
FIG. 19A is a SEM micrograph at low magnification of a protein (BSA) chip micro structure manufactured by the immobilizing device according to the present invention.
FIG. 19B is a SEM micrograph at high magnification of the protein (BSA) chip micro structure manufactured by the immobilizing device according to the present invention.

FIG. 19A is a scanning electron microscope (SEM) micrograph at low magnification of a protein (BSA) chip micro structure manufactured by the immobilizing device according to the present invention and FIG. 19B is a SEM micrograph at high magnification of the protein (BSA) chip micro structure manufactured by the immobilizing device according to the present invention. Although particle size is 0.2 μm to 1 μm as shown in FIGS. 19A and 19B, a chip composed of particles having a desired particle size can be manufactured by changing a vibration condition (i.e., driving voltage) of the atomizer.

Figure 20:
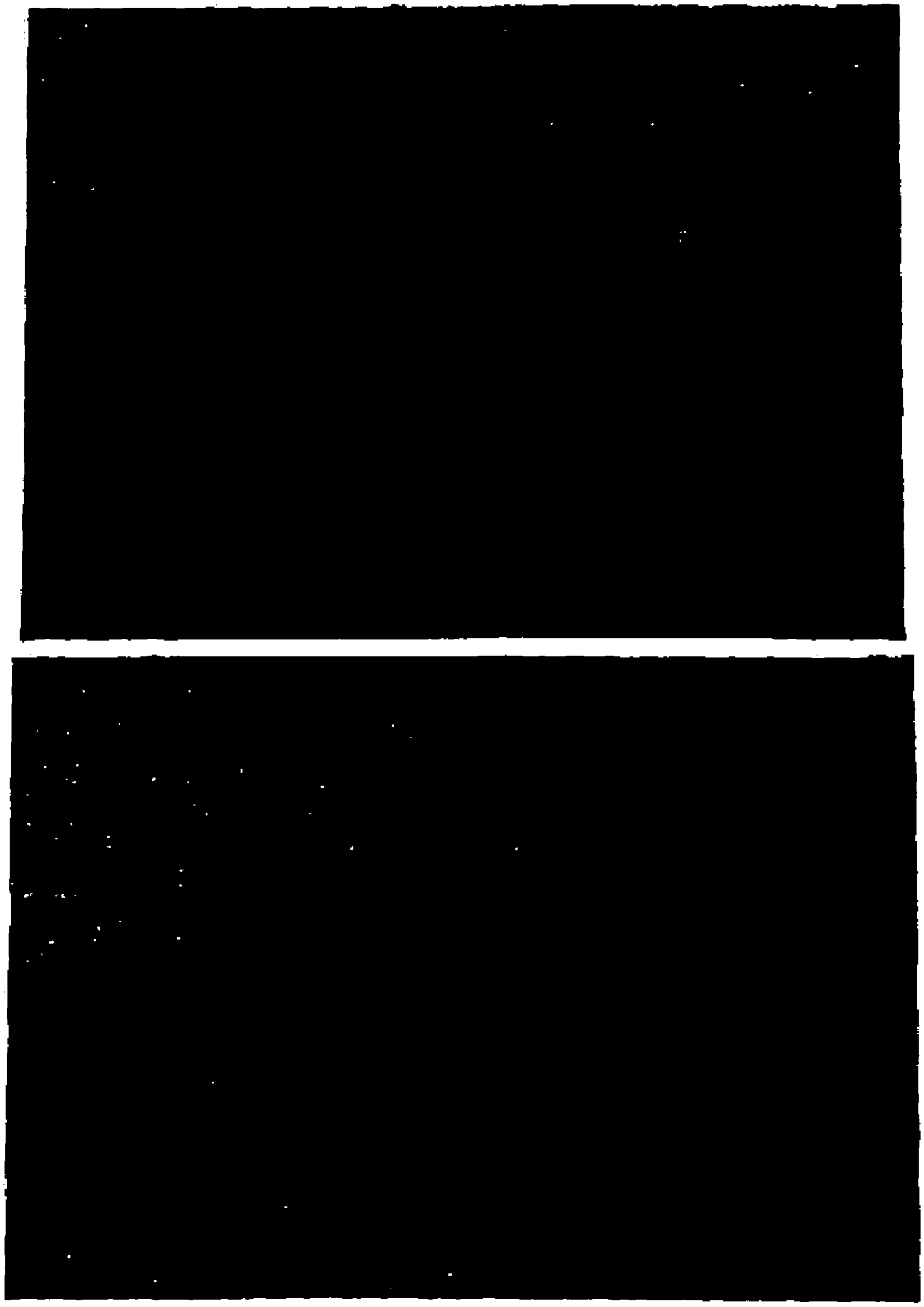
FIG. 20A is a proof photograph, obtained under normal illumination, showing degree of activity of a chip manufactured by the immobilizing device according to the present invention.
FIG. 20B is a proof photograph, obtained under dim illumination for easily observing luminescent conditions, illustrating degree of activity of a chip manufactured by the immobilizing device according to the present invention.

FIG. 20A is a proof photograph, obtained under normal illumination, showing degree of activity of a chip manufactured by the immobilizing device according to the present invention and FIG. 20B is a proof photograph, obtained under no illumination for easily observing luminescent conditions, illustrating degree of activity of a chip manufactured by the immobilizing device according to the present invention.

Using the immobilizing device according to the present invention, 40 μl of a luciferase solution (0.25 μg/μl) was atomized to be immobilized as a chip, and then the immobilized chip is dissolved in a reaction solution (luciferin solution) and luminescence status of the solution was observed. As shown in FIG. 20A, a target tube containing the solution dissolved the chip, which is manufactured by the immobilizing device according to the present invention is located at the upper left part of the image. There are provided other two tubes for comparison, a tube located at the upper right part of the image contains only a reaction solution (luciferin solution), and a tube located at the lower part of the image contains the solution dissolved the chip, which is manufactured by the immobilizing device according to the present invention, after one hour goes by after dissolved.

As shown in FIG. 20B, in the target tube located at the upper left, the luciferase (luminescent enzyme) reacted the luciferin (luminescent substrate) and as a result bioluminescence was generated, and this bioluminescence was observed. Namely, it has been found that functional activities of the luciferase can be retained due to the process according to the present invention. Additionally, it has been found that the tube for reference located at upper right part of the image was entirely non-luminescent. Furthermore, the tube located at lower part contained the solution, in which after one hour went by after the solution for the upper left tube was made, in this circumstance it has been found that there existed weak bioluminescence. Therefore, it has been found that functional activities of the luciferase can be "highly" retained due to the process according to the present invention.

In addition, luciferase used in this embodiment has a very low stability, if once the buffering agent is excluded, this substance instantly loses its activities, it is impossible to manufacture a chip of this substance using a conventional ESD method. In this way, according to the immobilizing device of the present invention, even if such a substance having a lower stability, since such a substance tin the presence of the buffering agent can be atomized and immobilized, this device has a great advantage.

Figure 21:
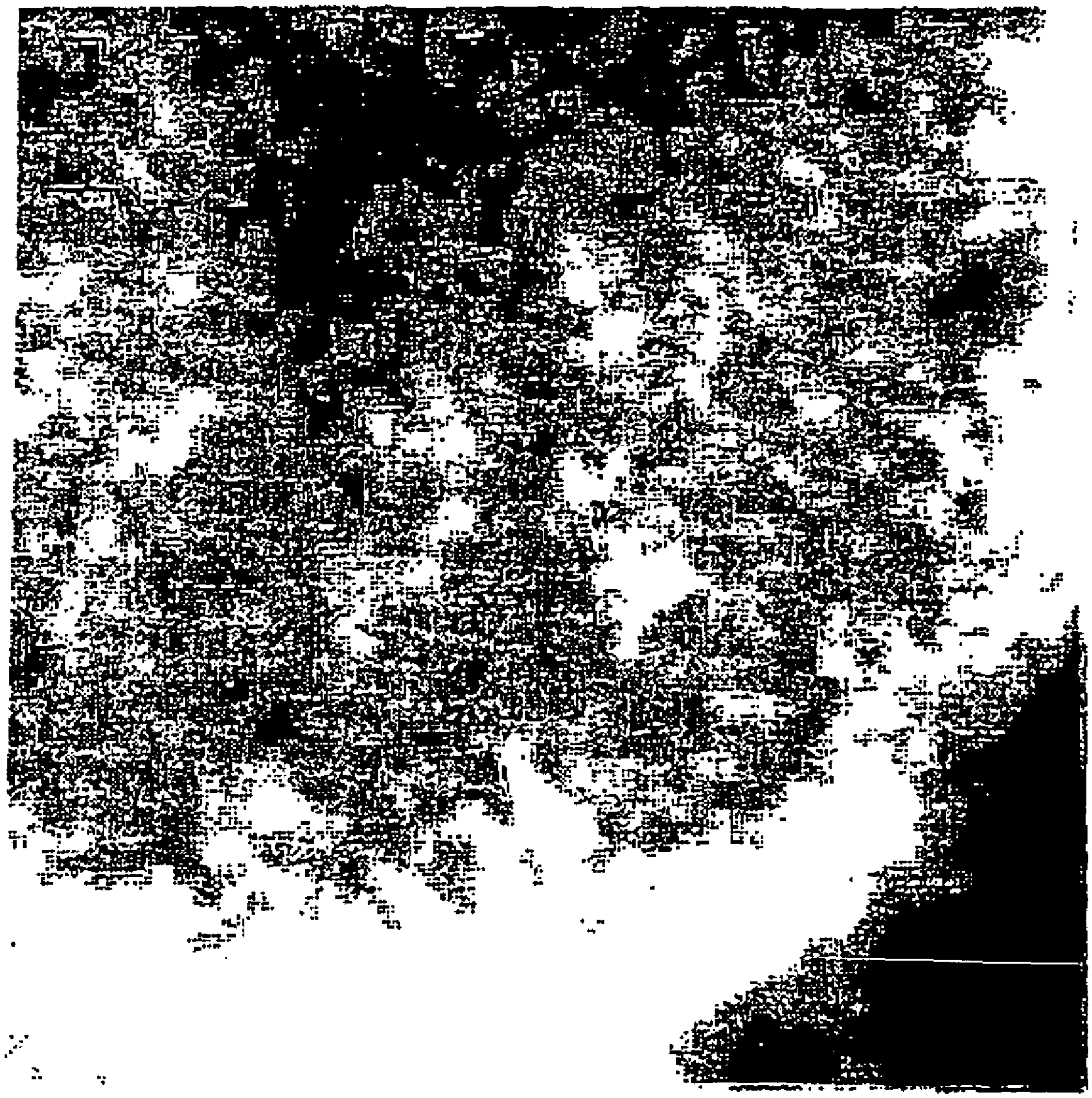
FIG. 21 is a photograph depicting degree of activity of a anti-mouse IgG chip manufactured by the immobilizing device according to the present invention.

FIG. 21 is a photograph depicting degree of activity of a anti-mouse IgG chip manufactured by the immobilizing device according to the present invention. Namely, this photograph is an image for evaluating a fluorescence intensity of anti-mouse IgG contained in the chip, which is manufactured such that anti-mouse IgG is atomized, cross-linked, and immobilized, to form a chip, and to react it. As shown in FIG. 21, it could be observed that there was emission of light by fluorescence (in the image, this area can be observed as white) over all of the chip. In this way, due to use of this immobilizing device, an anti-mouse IgG chip retaining its activities can be formed.

Figure 22:
FIGS. 22A and 22B are schematic diagrams, seen on cross section, for showing atomization phenomenon by means of only a vibration.
Figure 22:
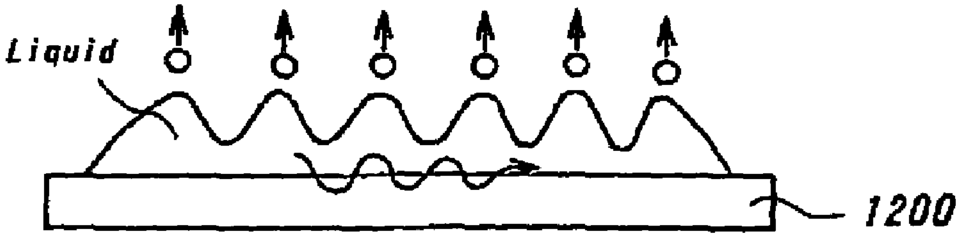

And now, the immobilizing device according to the present invention utilizes an atomizing phenomenon caused by "vibration" and "applying voltage", this phenomenon will be explained below. Firstly, as a prior art, an atomizing phenomenon caused by "vibration alone" will be described. FIGS. 22A and 22B are schematic diagrams, seen on cross section, for showing atomization phenomenon by means of only a vibration. Although FIG. 22A shows schematic diagram where weak vibration is excited, as shown in FIG. 22A, in a condition that there is liquid on a substrate 1200 such as a piezoelectric element or the like, when weak vibration is excited on the substrate 1200, the weak vibration is transmitted to the liquid, and thus small waves are generated on the liquid surface. However, when vibration is not sufficiently strong, liquid surface is ruffled slightly and atomizing does not occur.

However, although FIG. 22B shows schematic diagram where strong vibration is excited, as shown in FIG. 22B when there is provided sufficiently strong vibration, very big waves are generated on the liquid surface. At this time if movement velocity in the vicinity of the liquid surface is sufficiently high, a piece of the liquid is flied out as droplets while throwing off a binding force by a surface tension. In addition, although in the drawings vibration is expressed as surface acoustic waves (SAW), even if the vibration is in different vibration modes such as a travelling-wave, a bending wave, an axial vibration, or a lateral vibration, it can be conceived that the same interpretation is satisfied.

Figure 23:
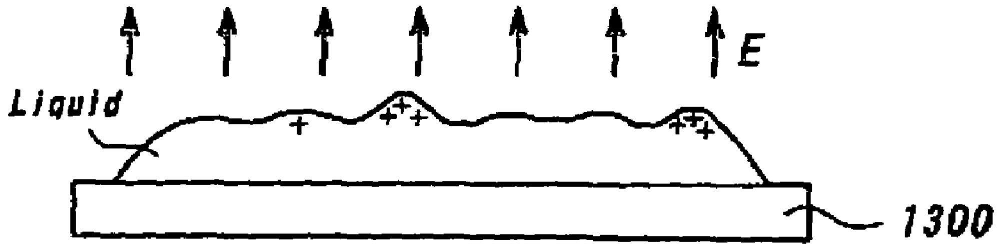
FIGS. 23A and 23B are schematic diagrams, seen on cross section, for depicting atomization phenomenon by means of only an applying electric field.
Figure 23:
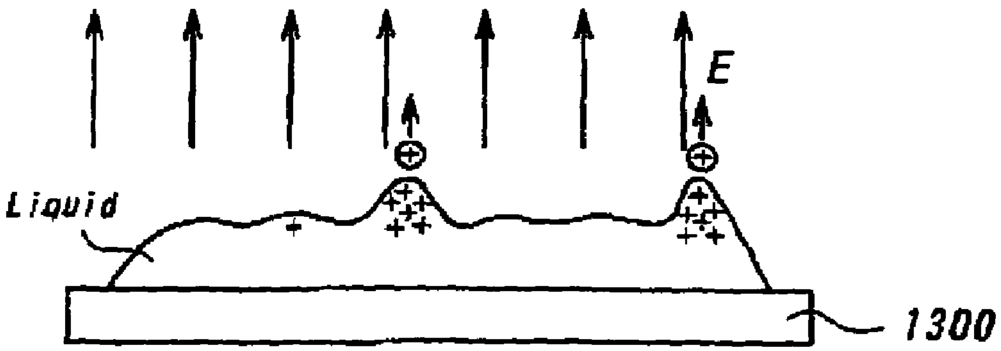

Secondly, an atomizing phenomenon (i.e., electro-splay) caused by "electric field alone" will be described FIGS. 23A and 23B are schematic diagrams, seen on cross section, for depicting atomization phenomenon by means of only an applying electric field. Although FIG. 23A shows schematic diagram where weak electrical field is applied, as shown in FIG. 23A, in a condition that there is liquid on a substrate 1300 such as a piezoelectric element or the like, when weak electric field (or voltage) is applied to the substrate 1300, in this circumstance the liquid surface is electrically charged, since the liquid surface is not completely isotropic, a part, win which collects the electric charges, is locally generated. However, if intensity of the electrical field is not efficiently high (that is weak electrical field), the liquid can not be atomized.

On the other hand, although FIG. 23B shows schematic diagram where strong electrical field is applied, as shown in FIG. 23B, in a condition that there is liquid on a substrate 1300 such as a piezoelectric element or the like, when sufficiently strong electric field (or voltage) is applied to the substrate 1300, a piece of the liquid is flied out as droplets toward the air (in direction of the electrical field) while throwing off a binding force by a surface tension due to electrostatic force, in which the electrical charges are subjected by the electrical field. However, in this circumstance amount of atomizing is very small, it is impossible to use the atomized file particles to immobilize them. Additionally, although, in order to charge the liquid, it is necessary that the substrate is made of a conductive material or there is provided electrodes in the liquid, or there is provided other electrodes at upper part of the Figs or the like for generating electrical field, these components are not shown.

Figure 24:
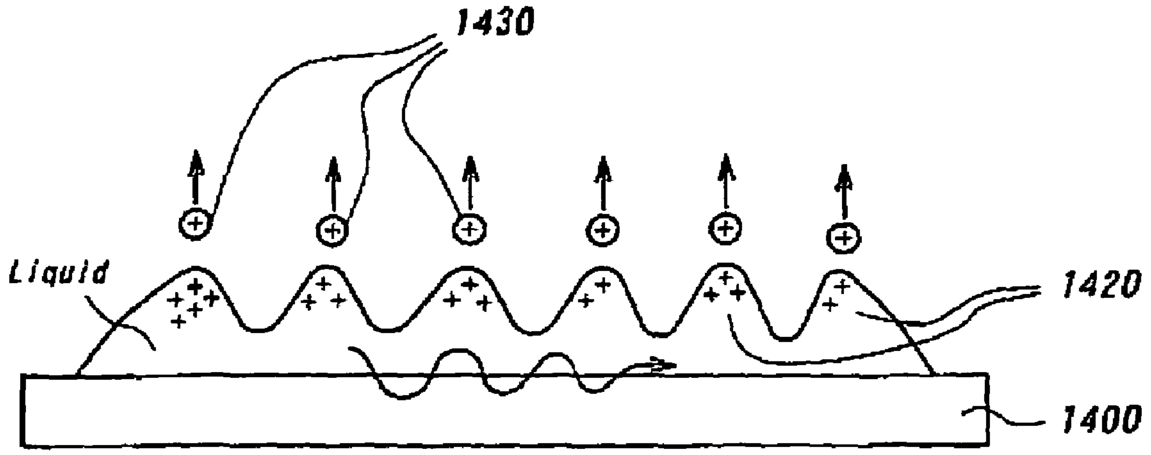
FIG. 24 is a schematic diagram, seen on cross section, for representing atomization phenomenon by synergistic effect caused by means of both a vibration and an applying electric field.

Finally, an atomizing phenomenon caused by synergistic effect caused by means of both "vibration" and "applying electric field" will be explained. FIG. 24 is a schematic diagram, seen on cross section, for representing atomization phenomenon by synergistic effect caused by means of both a vibration and an applying electric field. As shown in FIG. 24, if electrical field is applied during providing vibration to a substrate 1400, it gives rise to the phenomenon of focusing the electrical charges on the vicinity of the crests of the wave 1420 caused by the vibration. This phenomenon is caused by a physical lay that electrical charges focus on a point having a small value of curvature radius. As a result, due to that a piece of the liquid is subjected to the synergetic effect of both "movement energy" by the vibration and "electrostatic force" of the electrical charges by the electrical field, the pieces of the liquid can easily jump out of the liquid as charged droplets 1430 (Although in Fig. the charges of the droplets are positive, they can be negative).

In the phenomenon caused by "only electrical field", when a liquid has very high conductivity, since the electrical charges tend to distribute and local electrical charge concentration hardly occurs, practical sense it is impossible to perform electrostatic spraying in this condition. On the other band, in the method utilizing this combined effect, since the electrical charges focus on the near or vicinity of the crests of the wave 1420 caused by the vibration, even if the liquid to be atomized has high electrical conductivity a phenomenon of concentration of electrical charges occurs and thus atomizing can be performed. Additionally, even if there are provided "weak electrical field" and "weak vibration", atomization can be performed. Furthermore, the more intensity of the "electrical field" and/or "vibration" are applied, the more atomization speed or the more atomization efficiency can be obtained, and thus particle size of the atomized droplets could be decreased.

In the case of atomization of "only mechanical vibration" described above, after the droplets jumps out in the air, the droplets will fly using only its movement energy. However, in the case of the atomization by the combined effect, since the droplets 1430 are electrically charged, it is expected that it has an advantage that the droplets will split into pieces by electrical repulsive force within each droplets 1430. Furthermore, it is possible to focus the droplets 1430 on a desired point using the electrical field the droplets 1430, and to collect them.

As described above, due to the combined effect caused by that the technique for providing mechanical vibration by a piezoelectric element or the like to a liquid and a technique for applying electrical field are simultaneously performed, even if it is done under a harder condition, the atomization can efficiently and effectively be performed.

Figure 25:
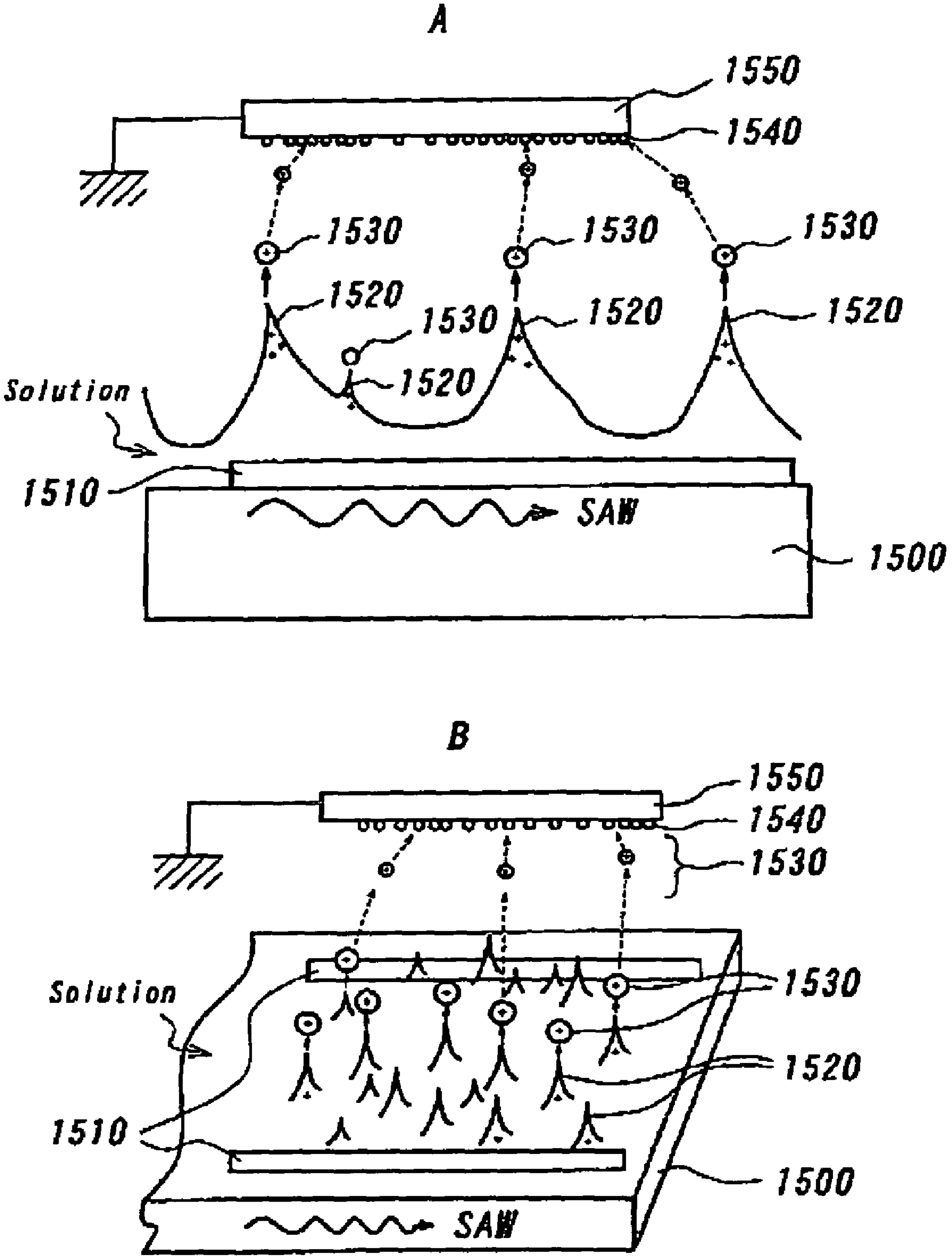
FIG. 25A is a schematic diagrams, seen on cross section, for schematically showing a principle of a atomizer in the immobilizing device according to the present invention.
FIG. 25B is a schematic perspective view depicting the atomizer of FIG. 25A.

FIG. 25A is a schematic diagrams, seen on cross section, for schematically showing a principle of a atomizer in the immobilizing device according to the present invention, and FIG. 25B is a schematic perspective view depicting the atomizer of FIG. 25A. Namely, these drawings are schematic diagram illustrating the immobilizing device using the atomization phenomenon of combined effect caused by both "vibration" and "applying electrical field". As shown in FIGS. 25A and 25B, an atomizer comprises a vibrating element 1500, and wires 1510 as a charging means disposed on the element. A predetermined driving voltage is supplied to the vibration element to generate a surface acoustic wave(s) (SAWs). When a protein solution is supplied onto the vibrating element, the solution receives the SAW from the vibrating element, waves as shown are generated, and to form an endless number of crests 1520 of wave in succession. In other words, a great number of prongs like a tip of a capillary are formed on the solution surface. On the other hand, the wires 1510 are connected to a high voltage power source (not shown), and a high voltage is applied to the solution. The electrical charges generated by this applying will focus on crests (prongs) of wave 1520, which are generated by the vibration, of the solution. A piece of the solution, on which the electrical charges focus on, will electrostatically jump out of the crests 1520 upward as charged minute particulate substances 1530. During the jumped out charged minute particulate substances 1530 fly to a substrate 1550 for immobilizing sample, which is grounded, a solvent(s) or water is dried off and thus the particles will decrease its particle size. Additionally, it may happen that the particulate substances 1530 split into pieces by electrical repulsive force within each particles 1530.

As a result, the particulate substances 1530 are immobilized on the substrate 1550 for immobilizing sample, which faces the vibrating element 1500 for immobilizing sample, in a dry form as spots 1540.

As described above, the present invention is a technique for ruffling the solution on the vibrating element substrate by vibrating, to form an endless number of the prong parts, and the same time for focusing electrical charges on the prong parts by applying a high voltage, and thereby the solution can be electstatically be atomized as electstatically charged minute particulate substances.

In this connection, it may happen that on the vibrating element there occurs an atomization caused by only the vibration, and the same time there occurs an atomization caused by only the applying the electrical field, other than the atomization by the electrostatic force.

Industrial Applicability

According to the immobilizing device of the present invention, since a sample solution is atomized by simultaneously applying mechanical vibration and charging, even if a solution in higher conductivity, that is, a solution without excluding the buffer agent is used, such a solution can be atomized, and as a result it is possible that a sample can be immobilized in a status retaining more highly activities thereof. For example, the present device can be used as a deposition device, or a microarray (DNA chip) manufacturing device.

Since the immobilizing device of the present invention uses no capillary, the present invention has the remarkable advantage that it is low cost and it is easy to maintain, because processing speed and atomizing efficiency can easily be increased by just extending an area or size of the vibrating element in this device.

What is claimed is:

1. An immobilizing device comprising:

a vibrating element for vibrating a solution or a solvent containing at least one sample, to form prongs of the solution or the solvent; and a charging device which is a separate unit from the vibrating element and disposed above the vibrating element with a spacing between the charging device and the vibrating element, the charging device being configured to contact the solution or the solvent, and to electrically charge the solution or the solvent in the prongs formed by the vibration of the vibrating element, wherein the charging device and the vibrating element are operated simultaneously to atomize the solution or the solvent by utilizing electrical charge concentration toward the prongs of the solution or the solvent formed by the vibration of the vibrating element into minute particulate substances whose activities and functionalities are kept, the device further comprises supporting means for supporting a substrate, disposed apart from the vibrating element, on which said charged minute particulate substances are deposited electrostatic forces, and said vibrating element comprises spreading means for spreading out said solution or solvent as a thin layer on the vibrating element.

2. The immobilizing device according to claim 1, wherein the device further comprises collecting means for collecting said atomized and charged minute particulate substances by electrostatic forces, and to direct said substances onto said substrate.

3. The immobilizing device according to claim 2, wherein said collecting means comprises one or more masks which are made of an insulating or dielectric material and disposed between the vibrating element and the substrate and/or one or more convergence electrodes disposed between the vibrating element and the substrate.

4. The immobilizing device according to claim 1, wherein the device further comprises means for regulating temperature of at least one of said vibrating element, said substrate, and said solution or solvent.

5. The immobilizing device according to claim 1, wherein said charging device comprises at least one of a conductive wire, a conductive membrane, a conductive mesh, and a device for emitting charged ions.

6. The immobilizing device according to claim 1, wherein the device further comprises liquid supplying means for feeding said solution or solvent onto said vibrating element in a predetermined rate of flow.

7. The immobilizing device according to claim 1, wherein at least a part of a surface of said vibrating element opposed to said substrate is subjected to a hydrophilic or hydrophobic treatment.

8. The immobilizing device according to claim 1, wherein the device further comprises particle size control means disposed between the vibrating element and the substrate for controlling sizes of said particulate substances.

9. The immobilizing device according to claim 1, wherein the device further comprises drying means for drying said particulate substances and wherein said drying means comprises at least one of means for supplying dry air, means for reducing pressure, and means for forming a vacuum.

10. The immobilizing device according to claim 1, wherein at least a part of a surface of said substrate is made of a conductive material and is grounded.

11. The immobilizing device according to claim 10, wherein said at least a part of the surface made of the conductive material has one or more desired pattern regions.

12. The immobilizing device according to claim 1, wherein said vibrating element is activated intermittently.

13. The immobilizing device according to claim 1, wherein said vibrating element is an ultrasonic transducer, an electrostatic transducer, a piezoelectric transducer, a magneto-striction transducer, an electrostriction transducer, or an electromagnetic transducer.

14. The immobilizing device according to claim 13, wherein said piezoelectric transducer is a mono-layer structure transducer, a multiplayer structure transducer, a single crystal transducer, a resonant transducer, a surface acoustic wave (SAW) transducer, a length vibration mode transducer, a thickness sheer mode transducer, a radial vibration mode transducer, a thickness vibration mode transducer, or a longitudinal vibration mode transducer.

15. The immobilizing device according to claim 14, wherein said SAW transducer comprises one or more inter digital transducers (IDTs).

16. The immobilizing device according to claim 15, wherein the device further comprises means for feeding said solution or solvent onto a region, at a distance from said IDTs, of said SAW transducer in a predetermined rate of flow, and to hold said fed solution or solvent on a predetermined region of said SAW transducer.

17. The immobilizing device according to claim 14, wherein said SAW transducer comprises one or more reflectors.

* * * * *